(12) United States Patent
Rosenbaum et al.

(10) Patent No.: US 10,758,267 B2
(45) Date of Patent: Sep. 1, 2020

(54) TROCAR ASSEMBLY WITH A CLEANING ELEMENT FOR USE DURING A LAPAROSCOPIC PROCEDURE

(71) Applicant: CareFusion 2200, Inc., San Diego, CA (US)

(72) Inventors: Joanna L. Rosenbaum, Evanston, IL (US); Jeanny Chung, Deerfield, IL (US); Patrick Hubbard, Vernon Hills, IL (US); Joseph Prybell, Mundelein, IL (US); Corrie Threlkeld, Vernon Hills, IL (US); Sara Tillman, Vernon Hills, IL (US); Brandon Toth, Vernon Hills, IL (US); Andrew P. VanDeWeghe, Grayslake, IL (US); Thomas Wilschke, Chicago, IL (US); Jesse Charles Darley, Madison, WI (US); Christopher Alan Harris, Madison, WI (US); Curtis B. Irwin, Madison, WI (US); Stephen A. Latham, Sun Prairie, WI (US); Daniel J. Lee, Princeton Junction, NJ (US); Douglas Rodenkirch, Sun Prairie, WI (US); Jeffrey R. Staszak, Deerfield, WI (US)

(73) Assignee: CareFusion 2200, Inc., San Diego, CA (US)

( * ) Notice: Subject to any disclaimer, the term of this patent is extended or adjusted under 35 U.S.C. 154(b) by 19 days.

(21) Appl. No.: 15/993,342

(22) Filed: May 30, 2018

(65) Prior Publication Data

US 2018/0344427 A1    Dec. 6, 2018

Related U.S. Application Data

(60) Provisional application No. 62/513,270, filed on May 31, 2017, provisional application No. 62/513,278, filed on May 31, 2017.

(51) Int. Cl.
*A61B 17/34* (2006.01)
*A61B 1/313* (2006.01)
(Continued)

(52) U.S. Cl.
CPC ...... *A61B 17/3421* (2013.01); *A61B 1/00089* (2013.01); *A61B 1/00091* (2013.01);
(Continued)

(58) Field of Classification Search
CPC . A61B 17/3421; A61B 17/3423; A61B 1/126; A61B 90/70
(Continued)

(56) References Cited

U.S. PATENT DOCUMENTS 5,274,874 A   1/1994 Cercone et al.
5,351,675 A   10/1994 Brodsky
(Continued)

FOREIGN PATENT DOCUMENTS

EP   2111782 A2   10/2009
EP   2111808 A2   10/2009
(Continued)

OTHER PUBLICATIONS

Office Action dated Jul. 11, 2019 pertaining to U.S. Appl. No. 15/993,276.
(Continued)

*Primary Examiner* — Si Ming Ku
(74) *Attorney, Agent, or Firm* — Dinsmore & Shohl LLP

(57) ABSTRACT

A trocar assembly includes a cannula having a proximal portion and an opposing distal portion. The distal portion is configured to extend into a patient body. The cannula defines an access channel between the proximal portion and the distal portion, wherein the access channel is configured to receive a scope such that the scope can be maneuvered through the access channel to a location within the patient (Continued)

body. A cleaning element at the distal portion is configured to contact at least a distal end of the scope.

22 Claims, 12 Drawing Sheets

(51) Int. Cl.
  *A61B 1/12* (2006.01)
  *A61B 90/70* (2016.01)
  *A61B 17/02* (2006.01)
  *A61B 1/00* (2006.01)
  *A61B 17/00* (2006.01)

(52) U.S. Cl.
  CPC ...... *A61B 1/00096* (2013.01); *A61B 1/00154* (2013.01); *A61B 1/126* (2013.01); *A61B 1/3132* (2013.01); *A61B 17/0218* (2013.01); *A61B 17/34* (2013.01); *A61B 17/3415* (2013.01); *A61B 17/3423* (2013.01); *A61B 90/70* (2016.02); *A61B 1/00135* (2013.01); *A61B 17/3474* (2013.01); *A61B 2017/00907* (2013.01); *A61B 2017/3437* (2013.01); *A61B 2090/701* (2016.02)

(58) Field of Classification Search
  USPC .................................................. 600/127, 204
  See application file for complete search history.

(56) References Cited

U.S. PATENT DOCUMENTS

| | | | |
|---|---|---|---|
| 5,365,267 A | 11/1994 | Edwards | |
| 5,382,297 A | 1/1995 | Valentine et al. | |
| 5,429,609 A | 7/1995 | Yoon | |
| 5,518,502 A | 5/1996 | Kaplan et al. | |
| 5,549,543 A | 8/1996 | Kim | |
| 5,643,227 A | 7/1997 | Stevens | |
| 5,651,757 A | 7/1997 | Meckstroth | |
| 5,842,971 A | 12/1998 | Yoon | |
| 5,880,779 A | 3/1999 | Rhynes | |
| 5,910,106 A | 6/1999 | Morgan et al. | |
| 5,916,145 A | 6/1999 | Chu et al. | |
| 5,980,493 A | 11/1999 | Smith et al. | |
| 6,197,041 B1 | 3/2001 | Schichman et al. | |
| 6,319,266 B1 | 11/2001 | Stellon et al. | |
| 6,482,181 B1 | 11/2002 | Racenet et al. | |
| 6,497,716 B1 | 12/2002 | Green et al. | |
| 6,685,630 B2 | 2/2004 | Sauer et al. | |
| 6,976,957 B1 | 12/2005 | Chin | |
| 6,981,966 B2 | 1/2006 | Green et al. | |
| 7,025,747 B2 | 4/2006 | Smith | |
| 7,294,136 B2 | 11/2007 | Dubrul et al. | |
| 7,367,960 B2 | 5/2008 | Stellon et al. | |
| 7,390,315 B2 | 6/2008 | Stellon et al. | |
| 7,537,563 B2 | 5/2009 | Temple | |
| 7,691,089 B2 | 4/2010 | Gresham | |
| 7,771,384 B2 | 8/2010 | Ravo | |
| 7,811,225 B2 | 10/2010 | Sauer et al. | |
| 7,811,251 B2 | 10/2010 | Wenchell et al. | |
| 7,988,670 B2 | 8/2011 | Smith | |
| 8,070,730 B2 | 12/2011 | Rockrohr | |
| 8,092,423 B2 | 1/2012 | Gresham | |
| 8,123,682 B2 | 2/2012 | Wenchell | |
| 8,152,717 B2 | 4/2012 | Gomez | |
| 8,202,290 B2 | 6/2012 | Smith | |
| 8,206,411 B2 | 6/2012 | Thompson et al. | |
| 8,211,135 B2 | 7/2012 | Heinrich et al. | |
| 8,223,193 B2 | 7/2012 | Zhao et al. | |
| 8,241,251 B2 | 8/2012 | Gresham | |
| 8,257,253 B2 | 9/2012 | Piskun | |
| 8,257,254 B2 | 9/2012 | Piskun | |
| 8,257,315 B2 | 9/2012 | Franer et al. | |
| 8,267,896 B2 | 9/2012 | Hartoumbekis et al. | |
| 8,394,018 B2 | 3/2013 | Piskun | |
| 8,449,460 B2 | 5/2013 | Duke et al. | |
| 8,458,971 B2 | 6/2013 | Winterowd et al. | |
| 8,491,545 B2 | 7/2013 | Shelton, IV | |
| 8,496,622 B2 | 7/2013 | Shelton, IV | |
| 8,535,220 B2 | 9/2013 | Mondschein | |
| 8,636,686 B2 | 1/2014 | Minnelli et al. | |
| D700,326 S | 2/2014 | Minnelli et al. | |
| 8,708,889 B2 | 4/2014 | Feuer et al. | |
| 8,726,037 B2 | 5/2014 | Franer | |
| 8,728,109 B2 | 5/2014 | Piskun | |
| 8,764,648 B2 | 7/2014 | Piskun | |
| 8,771,307 B2 | 7/2014 | Franer | |
| 8,870,747 B2 | 10/2014 | Moreno, Jr. et al. | |
| 8,911,463 B2 | 12/2014 | Fischvogt | |
| 8,932,249 B2 | 1/2015 | Parihar et al. | |
| 8,961,552 B2 | 2/2015 | Fischvogt et al. | |
| 8,968,250 B2 | 3/2015 | McGinley et al. | |
| 9,039,604 B2 | 5/2015 | Yoshida | |
| 9,078,562 B2 | 7/2015 | Poll et al. | |
| D736,926 S | 8/2015 | Minnelli et al. | |
| 9,211,059 B2 | 12/2015 | Drach et al. | |
| 9,265,899 B2 | 2/2016 | Albrecht et al. | |
| 9,289,115 B2 | 3/2016 | Dang et al. | |
| D753,303 S | 4/2016 | Dannaher | |
| 9,314,266 B2 | 4/2016 | Kahle et al. | |
| 9,314,267 B2 | 4/2016 | Piskun et al. | |
| 9,358,040 B2 | 6/2016 | Kahle et al. | |
| 2002/0022762 A1 | 2/2002 | Beane et al. | |
| 2002/0065450 A1 | 5/2002 | Ogawa | |
| 2003/0139649 A1 | 7/2003 | Kasahara et al. | |
| 2005/0043683 A1 | 2/2005 | Ravo | |
| 2006/0293559 A1 | 12/2006 | Grice | |
| 2008/0194915 A1 | 8/2008 | Blackhurst et al. | |
| 2008/0200765 A1 | 8/2008 | Mondschein | |
| 2008/0306335 A1 | 12/2008 | Lau et al. | |
| 2009/0112057 A1 | 4/2009 | Kammer et al. | |
| 2009/0240111 A1 | 9/2009 | Kessler | |
| 2009/0270686 A1 | 10/2009 | Duke et al. | |
| 2009/0270818 A1 | 10/2009 | Duke | |
| 2010/0012152 A1 | 1/2010 | Hansen | |
| 2011/0149057 A1 | 6/2011 | Beck et al. | |
| 2012/0101337 A1 | 4/2012 | Clark et al. | |
| 2012/0101338 A1 | 4/2012 | O'Prey | |
| 2012/0178995 A1 | 7/2012 | Newton, IV | |
| 2012/0187104 A1 | 7/2012 | Heymann et al. | |
| 2013/0041230 A1 | 2/2013 | Hartoumbekis et al. | |
| 2013/0053639 A1 | 2/2013 | Ihde, II | |
| 2013/0085329 A1 | 4/2013 | Morrissette et al. | |
| 2013/0102843 A1 | 4/2013 | Feuer et al. | |
| 2013/0150670 A1 | 6/2013 | O'Prev et al. | |
| 2014/0171739 A1 | 6/2014 | Nguyen | |
| 2014/0215736 A1* | 8/2014 | Gomez ............. A61B 1/00154 15/104.05 |
| 2014/0235944 A1 | 8/2014 | Feuer et al. | |
| 2014/0249370 A1 | 9/2014 | Hurst | |
| 2015/0105626 A1 | 4/2015 | Kleyman | |
| 2015/0190041 A1 | 7/2015 | Suehara et al. | |
| 2015/0201826 A1 | 7/2015 | Hsu et al. | |
| 2015/0282695 A1 | 10/2015 | Tay et al. | |
| 2016/0015573 A1 | 1/2016 | Ihde, III | |
| 2016/0113484 A1 | 4/2016 | Nakaguchi | |
| 2016/0166135 A1 | 6/2016 | Fiset | |
| 2016/0317006 A1 | 11/2016 | Gomez et al. | |
| 2018/0035988 A1 | 2/2018 | Lau | |
| 2019/0191982 A1 | 6/2019 | Fiset | |

FOREIGN PATENT DOCUMENTS

| | | |
|---|---|---|
| EP | 2113215 A1 | 11/2009 |
| EP | 2193742 A1 | 6/2010 |
| EP | 2238928 A1 | 10/2010 |
| EP | 2111782 B1 | 8/2016 |
| JP | 2007105314 A | 4/2007 |
| WO | 2008030256 A1 | 3/2008 |
| WO | WO2010/011563 A3 | 7/2009 |
| WO | WO2010/011563 A2 | 1/2010 |
| WO | WO2013/012790 A2 | 7/2012 |
| WO | WO2013/012790 A3 | 7/2012 |

(56) References Cited

FOREIGN PATENT DOCUMENTS

WO    WO2013/063153 A2    5/2013
WO    WO2014/185334 A1    5/2014
WO    2018093817 A1    5/2018

OTHER PUBLICATIONS

International Search Report and Written Opinion in Application No. PCT/US2018/020850, dated May 17, 2018, 12 pages.
International Search Report and Written Opinion in Application No. PCT/US2018/020856, dated May 17, 2018, 15 pages.
International Search Report and Written Opinion in Application No. PCT/US2018/020853, dated Jun. 18, 2018, 16 pages.
International Preliminary Report on Patentability dated Dec. 12, 2019 pertaining to International PCT Application PCT/US2018/035191.
International Preliminary Report on Patentability dated Dec. 12, 2019 pertaining to International PCT Application PCT/US2018/035206.
International Preliminary Report on Patentability dated Dec. 12, 2019 pertaining to International PCT Application PCT/US2018/035199.

* cited by examiner

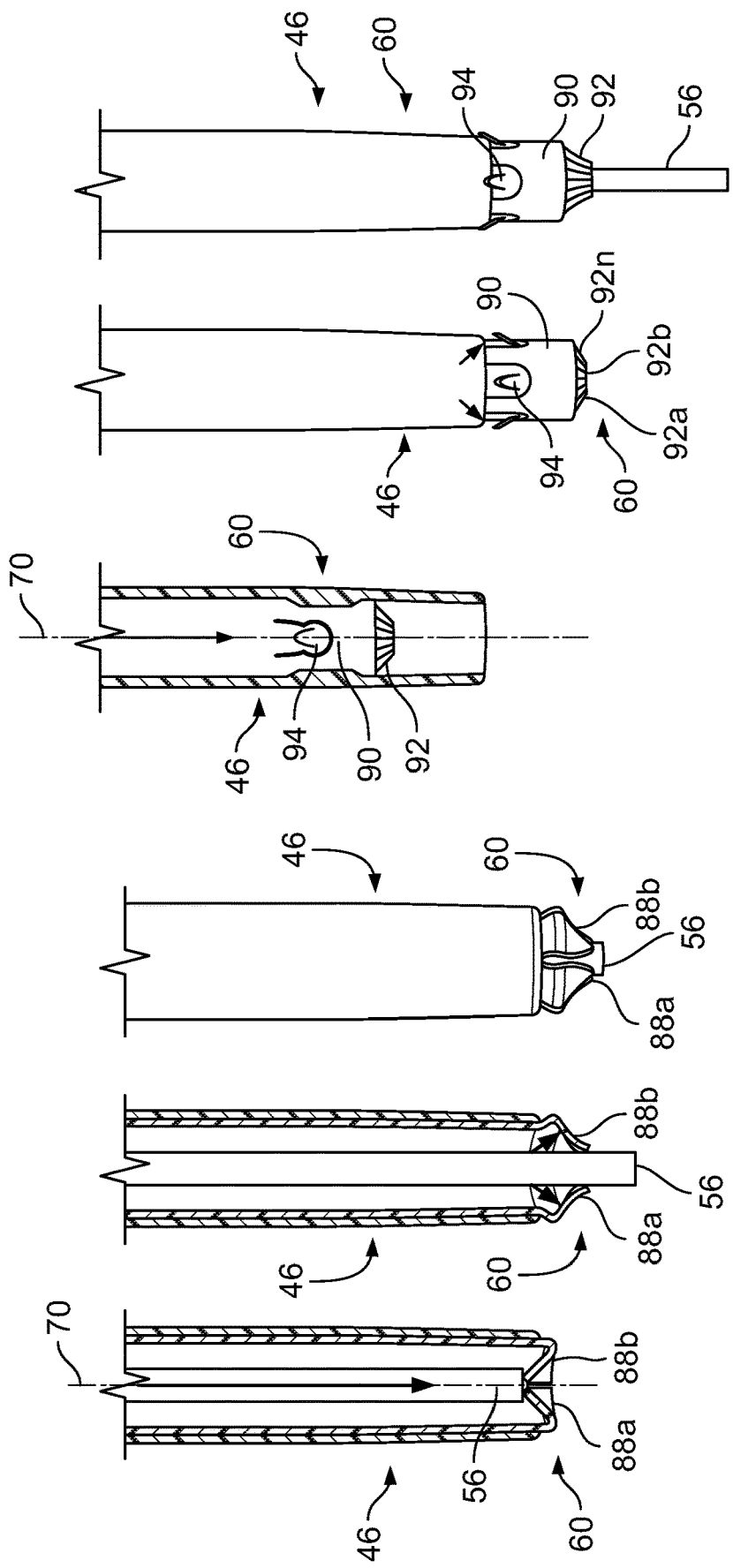

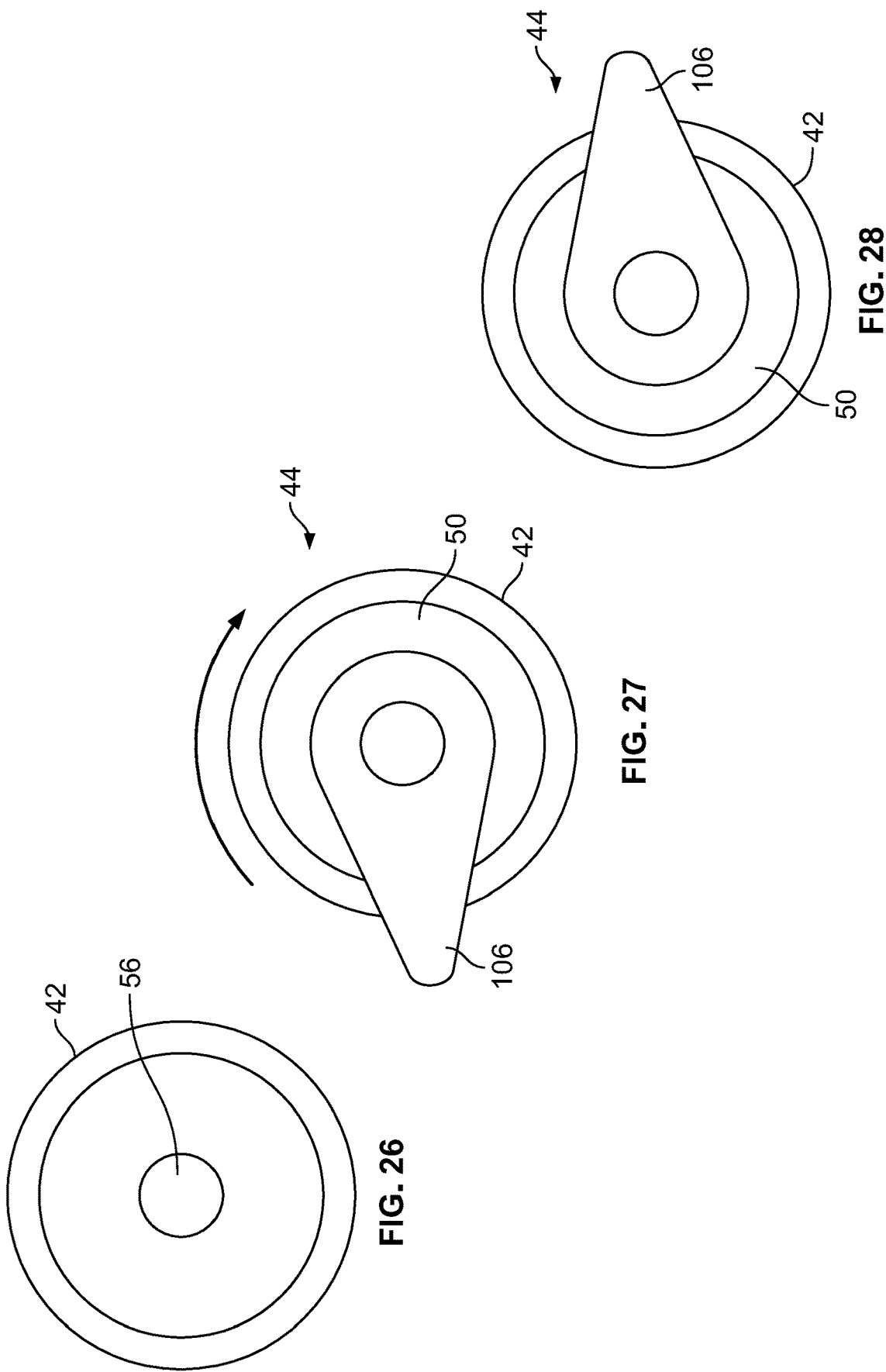

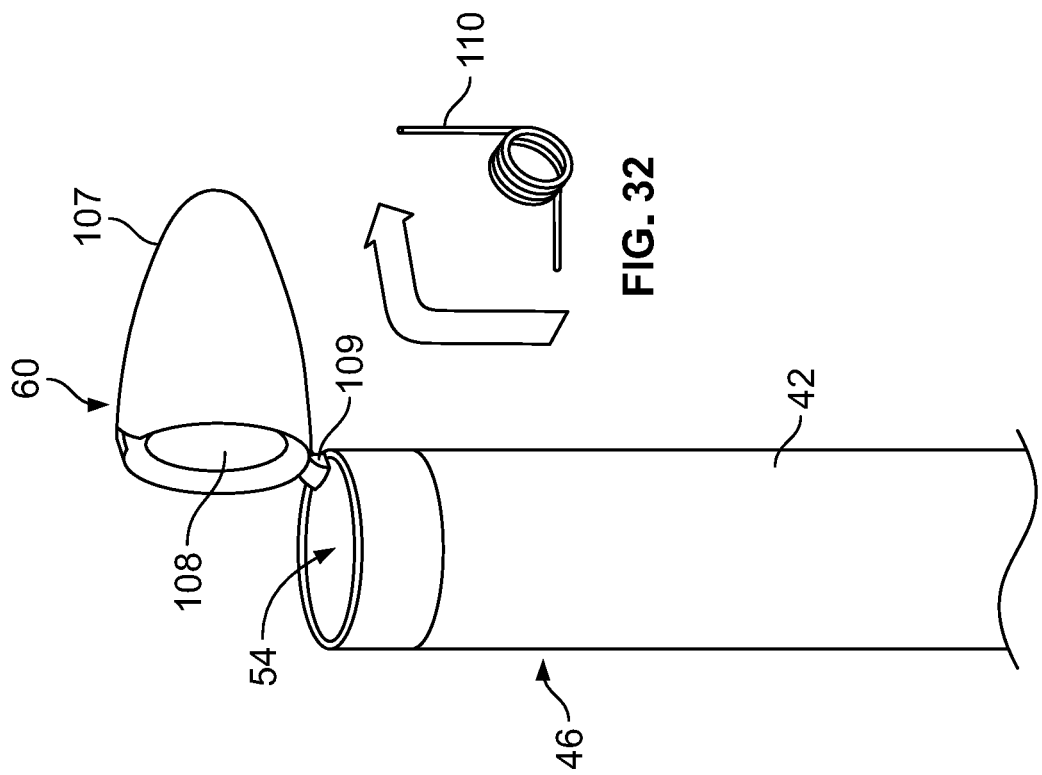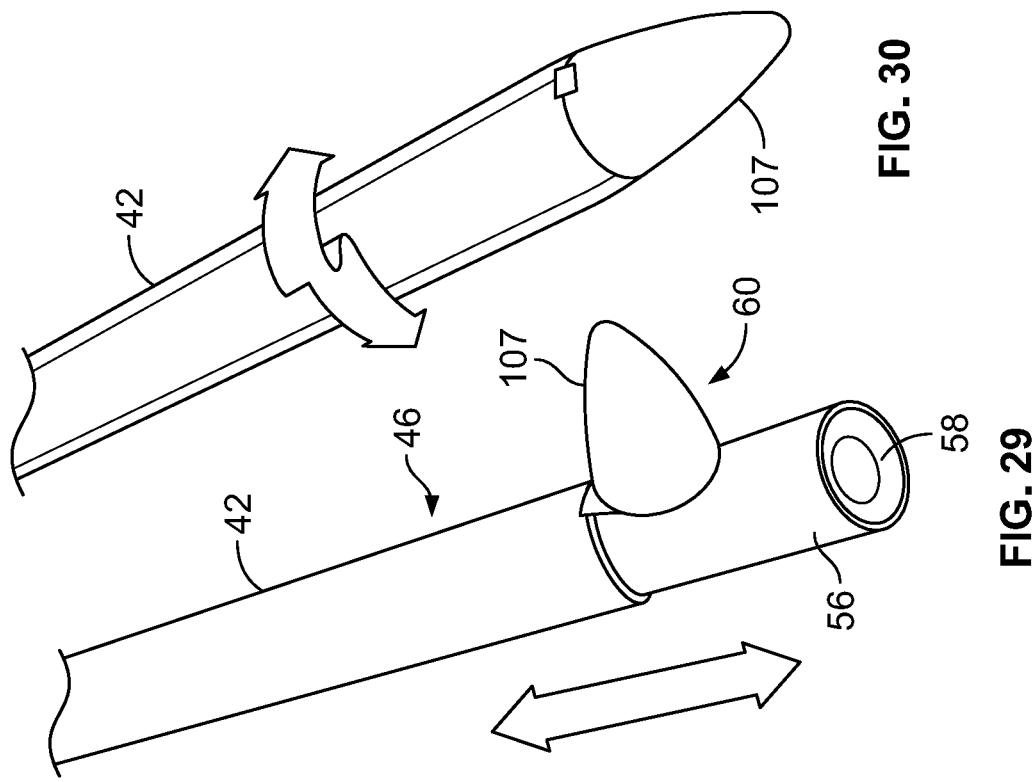

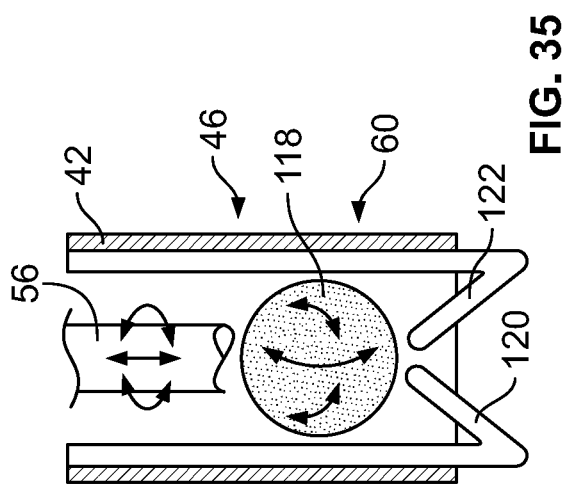
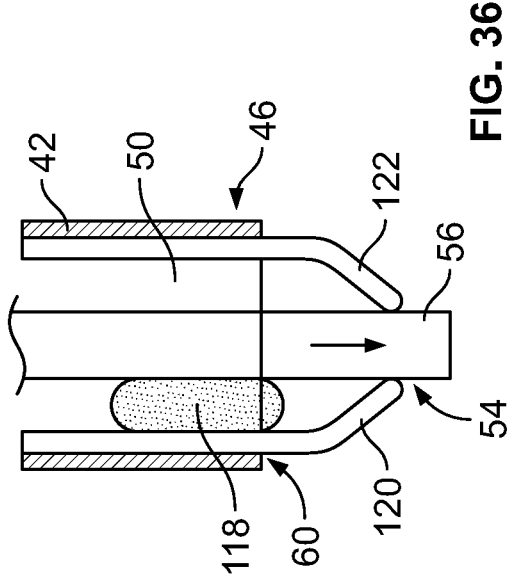
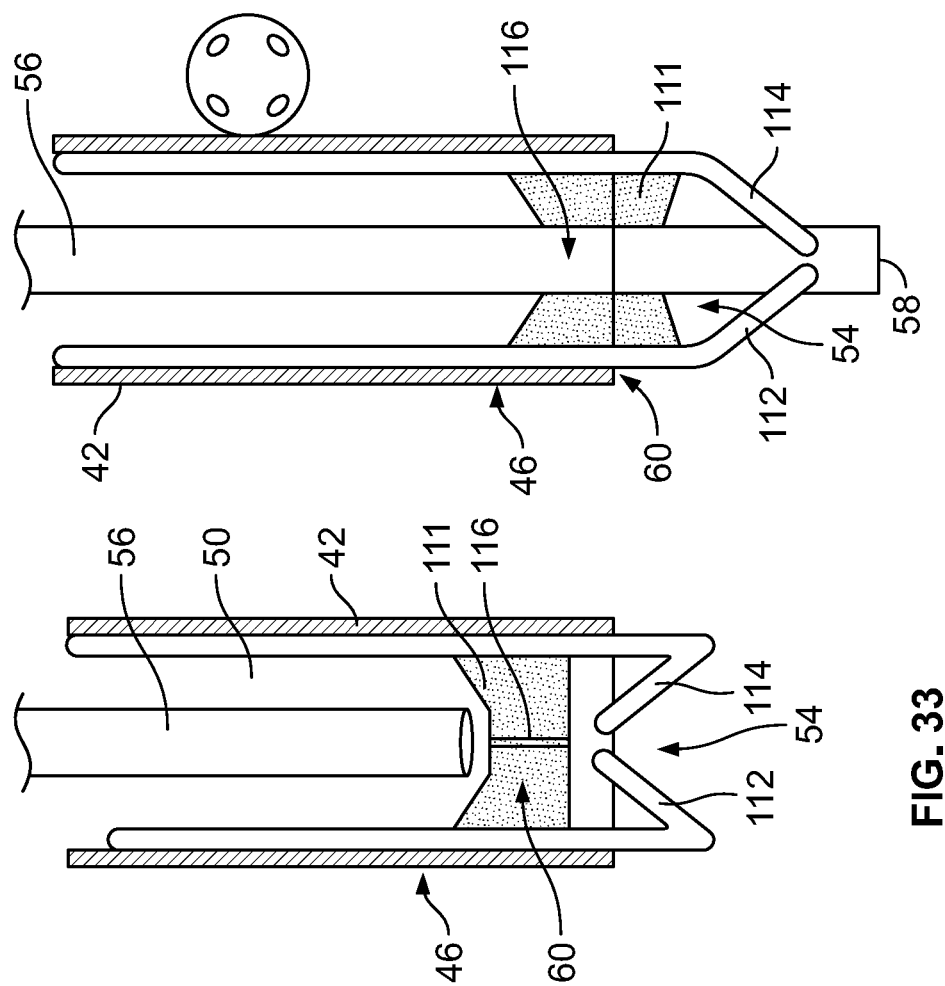

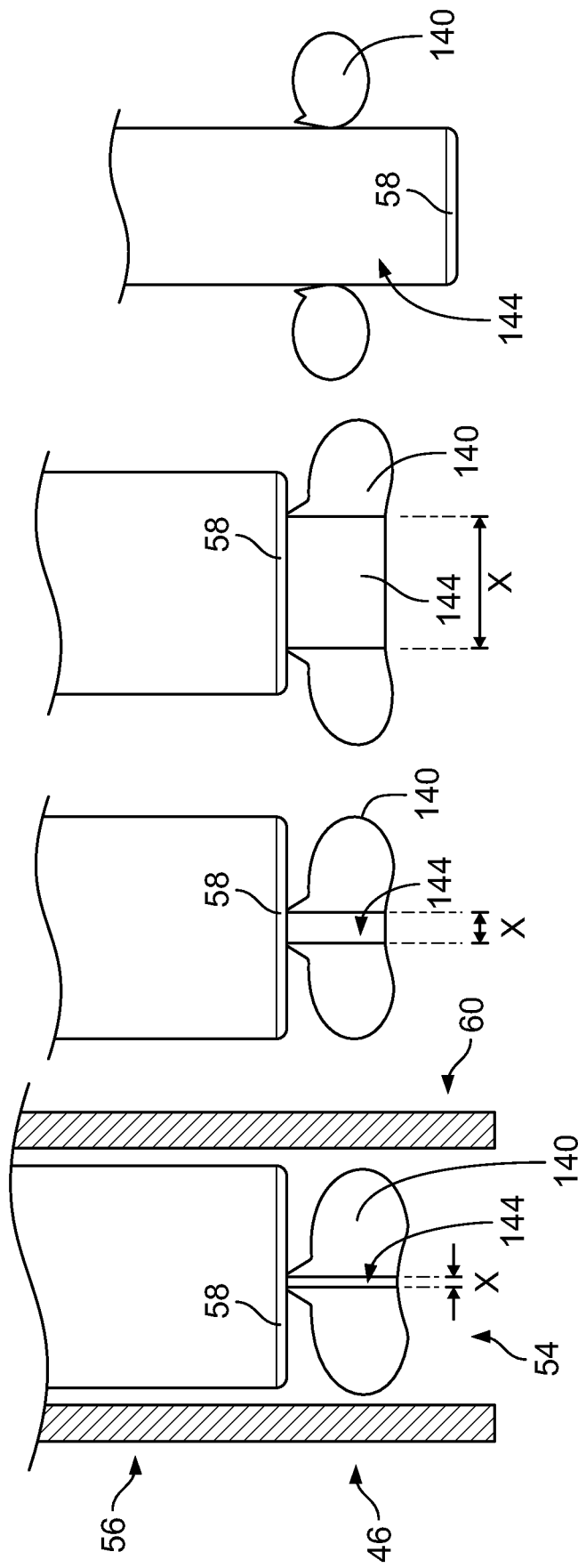

TROCAR ASSEMBLY WITH A CLEANING ELEMENT FOR USE DURING A LAPAROSCOPIC PROCEDURE

RELATED APPLICATIONS

This application claims the benefit of U.S. Provisional Application No. 62/513,270, filed May 31, 2017, and U.S. Provisional Application No. 62/513,278, filed May 31, 2017, each of which is herein incorporated by reference in its entirety. Further, each of the following applications, filed on Mar. 7, 2017, is herein incorporated by reference in its entirety: U.S. patent application Ser. No. 15/452,169, U.S. patent application Ser. No. 15/452,211, and U.S. patent application Ser. No. 15/452,246.

FIELD OF TECHNOLOGY

The present disclosure relates generally to trocar assemblies and related devices, and more specifically, to trocar assemblies which can be utilized in laparoscopic medical procedures.

BACKGROUND

Laparoscopic surgery is a minimally-invasive surgical technique typically performed with the assistance of one or more medical instruments inserted through a small incision in a patient's body. Laparoscopic surgery is often preferred to traditional and more invasive surgical procedures because of the reduced frequency and degree of certain postoperative side effects, such as postoperative pain, swelling, internal bleeding, and infection risk. The minimally-invasive nature of laparoscopic procedures may also result in decreased recovery times and shorter hospital stays.

Typical medical devices utilized during laparoscopic procedures have instruments mounted on an elongated metal or plastic body that are inserted into the patient's body and maneuvered to a target area within a body cavity (e.g., the abdominal, pelvic, thoracic, or chest cavity, where insufflation may be used to provide additional space in which to maneuver, which requires a fluid-patient barrier to maintain insufflation pressure in the cavity). One or more trocar assemblies are typically first inserted into the patient body at an incision site (for each), and the instruments access the patient body through the trocar assembly(ies).

Often, a medical device including a camera or other image-transmitting device is inserted through a trocar to transmit one or more images or a live video feed from within the body cavity to a medical professional (such as the surgeon). The device may be referred to as a scope or a laparoscope, and its transmission may guide the medical professional's actions during the laparoscopic procedure.

A problem typically experienced during laparoscopic procures involves a compromised image or video feed due to an obstructed lens of the laparoscope. This obstruction may be caused by condensation (e.g., fog) and/or debris such as bodily fluids or displaced tissue encountered by the lens during the procedure. Such obstruction is problematic because the lens of the laparoscope preferably remains contained in a pressurized and sterile environment (e.g., insufflated body cavity), and removing the lens from that environment for cleaning purposes may cause lengthy interruptions prolonging patient anesthesia and increasing a risk of compromised sterility.

SUMMARY

In one aspect, a trocar assembly includes a proximal portion. A cannula extends between the proximal portion and a distal portion of the trocar assembly opposite the proximal portion. The distal portion is configured to extend into a patient body. The cannula defines an access channel between a first opening at the proximal portion and a second opening at the distal portion, wherein the access channel is configured to receive a scope such that the scope can be maneuvered through the access channel to a location within the patient body. A cleaning element at the distal portion is configured to contact at least a distal end of the scope with the cleaning element in a first position.

In another aspect, a trocar assembly includes a cannula having a proximal portion and an opposing distal portion. The distal portion is configured to extend into a patient body. The cannula defines an access channel between the proximal portion and the distal portion, wherein the access channel is configured to receive a scope such that the scope can be maneuvered through the access channel to a location within the patient body. A cleaning element at the distal portion is configured to contact at least a distal end of the scope.

In yet another aspect, a method for cleaning a distal end of a scope positioned within an access channel of a trocar includes coupling a cleaning element at a distal portion of a cannula of the trocar assembly. The distal portion is configured to extend into a patient body. The cannula defines an access channel between a first opening at the proximal portion and a second opening at the distal portion, wherein the access channel is configured to receive a scope such that the scope can be maneuvered through the access channel to a location within the patient body. At least a distal end of the scope is cleaned with the cleaning element by moving the cleaning element with respect to the distal end of the scope.

BRIEF DESCRIPTION OF THE DRAWINGS

FIG. 14 is a sectional view of a distal portion of an example trocar assembly with a cleaning element in a first position in accordance with certain example embodiments;

FIG. 15 is a sectional view of the distal portion of the example trocar assembly shown in FIG. 14 with the cleaning element in a second position;

FIG. 16 is a plan view of the distal portion of the example trocar assembly of FIG. 14 with the cleaning element in the second position;

FIG. 17 is a sectional view of a distal portion of an example trocar assembly with a cleaning element in a retracted position in accordance with certain example embodiments;

FIG. 18 is a plan view of the distal portion of the example trocar assembly shown in FIG. 17 with the cleaning element in a first position;

FIG. 19 is a plan view of the distal portion of the example trocar assembly of FIG. 17 with the cleaning element in a second position;

FIGS. 26-28 are top views of the example trocar assembly shown in FIGS. 23-25 in accordance with certain example embodiments;

FIG. 29 is a perspective view of a distal portion of an example trocar assembly with a cleaning element in a second position in accordance with certain example embodiments;

FIG. 30 is a perspective view of the distal portion of the example trocar assembly shown in FIG. 29 with the cleaning element in a first position;

FIG. 31 is a perspective view of the distal portion of the example trocar assembly of FIG. 29 with the cleaning element in the second position;

FIG. 32 is a perspective view of a biasing element of the example trocar assembly of FIG. 29;

FIG. 33 is a sectional view of a distal portion of an example trocar assembly with a cleaning element in a first position in accordance with certain example embodiments;

FIG. 34 is a sectional view of the distal portion of the example trocar assembly shown in FIG. 33 with the cleaning element in a second position;

FIG. 35 is a sectional view of a distal portion of an example trocar assembly with a cleaning element in a first position in accordance with certain example embodiments;

FIG. 36 is a sectional view of the distal portion of the example trocar assembly shown in FIG. 35 with the cleaning element in a second position;

FIG. 37 is a sectional view of a distal portion of an example trocar assembly with a cleaning element in a first position, in accordance with certain example embodiments;

FIG. 38 is a sectional view of the distal portion of the example trocar assembly shown in FIG. 37 as the cleaning element moves from the first position to a second position;

FIG. 39 is a sectional view of the distal portion of the example trocar assembly shown in FIG. 37 as the cleaning element moves from the first position to the second position; and FIG. 40 is a sectional view of the distal portion of the example trocar assembly shown in FIG. 37 with the cleaning element in the second position.

DETAILED DESCRIPTION

Figure 2:
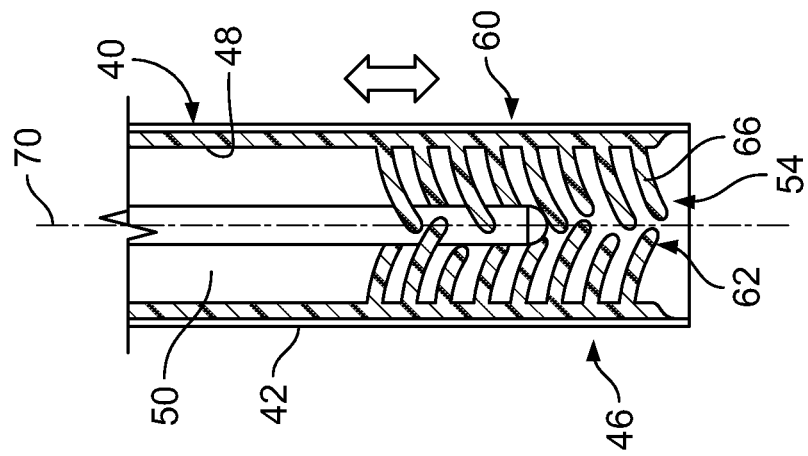
FIG. 2 is a sectional view of a distal portion of an example trocar assembly in accordance with certain example embodiments.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings may or may not be to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry and/or governmental standards (e.g., ASTM, ANSI, IEEE, HIPAA, FDA standards) is defined as complying with the currently published standards as of the original filing date of this disclosure concerning the units, measurements, and testing criteria communicated by those standards unless expressly otherwise defined herein.

The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

In example embodiments, such as described herein, a trocar assembly includes a proximal portion. A cannula extends between the proximal portion and a distal portion of the trocar assembly opposite the proximal portion. The distal portion of the trocar assembly is configured to extend into a patient body. The cannula defines or forms an access channel between a first or proximal opening at the proximal portion and a second or distal opening at the distal portion. The access channel is configured to receive a scope such that the scope can be maneuvered through the access channel to extend distally from the distal portion of the trocar assembly at a location within the patient body. A cleaning element is positioned at or coupled to the distal portion. The cleaning element is configured to contact at least a distal end of the scope with the cleaning element in a first position to periodically clean at least the distal end of the scope, e.g., a lens of an imaging device at the distal end of the scope, to remove condensation (e.g., fog) and/or debris, such as bodily fluids or displaced tissue, from the lens during the procedure. In certain example embodiments, the cleaning element is configured to clean an entire distally facing surface of the lens, e.g., by temporarily occluding the access channel at or near the distal opening. With the cleaning element contacting the distally facing surface of the lens a complete cleaning of the entire lens surface can be accomplished.

In example embodiments, the cleaning element is movable between a first or cleaning position and a second position allowing the scope to freely move in a proximal direction and/or a distal direction within the access channel. In the first position, the cleaning element contacts at least the distal portion of the scope with the scope positioned in the access channel to clean desired portions of the scope, e.g., the lens. In certain example embodiments, the cleaning element extends radially inward toward a longitudinal axis of the cannula in the first position. In the second position, the cleaning element may extend distally outward from an opening at the distal portion. In certain embodiments, an actuator at the proximal portion of the cannula is operatively coupled to the cleaning element and configured to move the cleaning element between the first position and the second position.

In certain example embodiments, the cleaning element includes a plurality of members, e.g., a plurality of brushes, bristles, fingers, leaflets, wipers, pads, projections, or any combination thereof, extending radially inward toward a longitudinal axis of the cannula such that the plurality of members contact the scope with the scope positioned in the access channel. The plurality of members may be biased radially inward toward the longitudinal axis of the cannula to allow the members in the first position to contact the scope. The members may be formed of a compliant or flexible material such that each member is movable upon contacting the scope, e.g., to allow the scope to move through the access channel without undesirable contact with or interference from the members, while providing sufficient resilience to facilitate cleaning the distal end of the scope, e.g., the lens.

In certain example embodiments, each member extends from an inner wall of the cannula defining the access channel toward the longitudinal axis of the cannula. Alternatively or additionally, the members are formed at the distal end of the cannula to extend distally from the distal portion of the cannula. For example, the members may be formed or positioned annularly about a distal opening of the access channel at the distal portion of the cannula.

Figure 1:
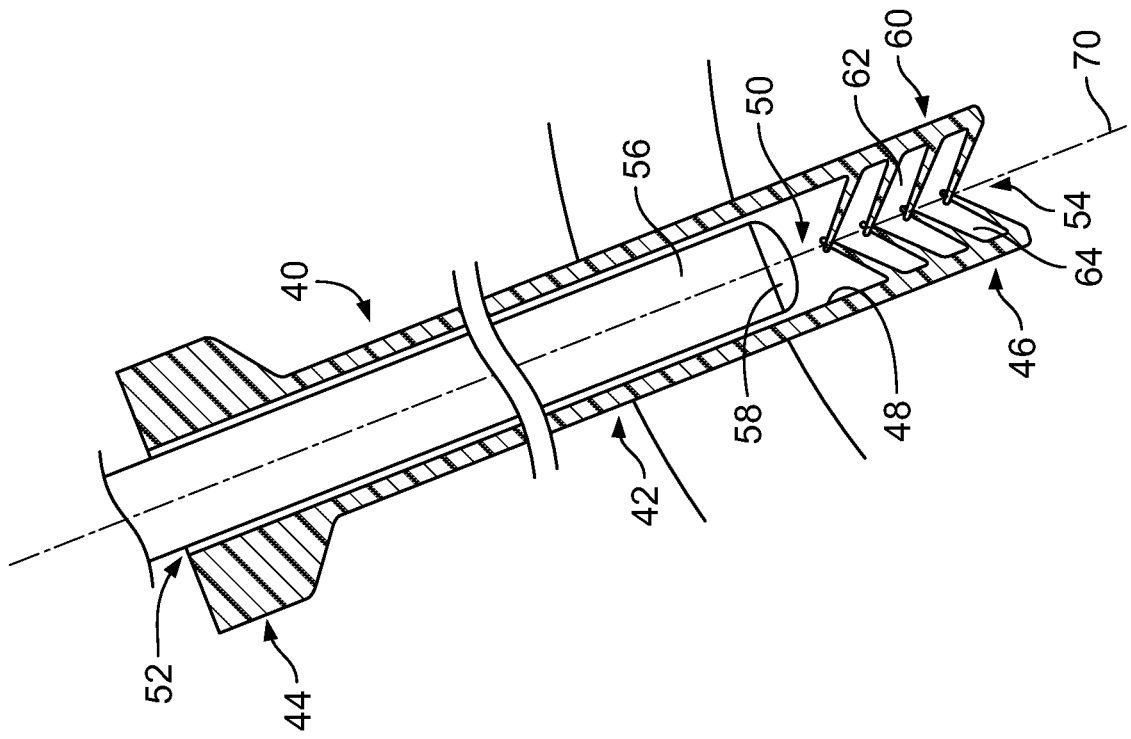
FIG. 1 is a sectional view of an example trocar assembly for use during a laparoscopic procedure in accordance with certain example embodiments.

Referring to FIGS. 1-40 and, initially to FIG. 1, a trocar assembly 40 includes a cannula 42 having a proximal portion 44 and an opposing distal portion 46. Distal portion 46 is configured to extend into a patient body to assist with performing minimally-invasive surgical procedures including, for example, laparoscopic surgical procedures. An inner wall 48 of cannula 42 forms or defines at least a portion of an access channel 50 that extends between a first or proximal opening 52 at proximal portion 44 and an opposing second or distal opening 54 at distal portion 46. Access channel 50 is configured to receive a scope, e.g., scope 56 having lens 58 shown in FIG. 1, such that scope 56 can be maneuvered through access channel 50 to a location within the patient body. A cleaning element 60 is operatively coupled to cannula 42 at distal portion 46. Cleaning element 60 is configured to contact at least a distal end of scope 56.

In example embodiments, cleaning element 60 comprises one or more members 62, e.g., a plurality of members 62, configured to clean lens 58 upon contact of members 62 with lens 58. Suitable members 62 include, without limitation, one or more, e.g., a plurality of, brushes, bristles, fingers, leaflets, wipers, pads, projections, or any combination thereof. In certain example embodiments, each member 62 is made or formed of a suitable flexible or compliant material to allow each member 62 to move upon contacting scope 56 to allow scope 56 to freely move through access channel 50 as controlled by the user, e.g., the surgeon. While each member 62 may be flexible or compliant, each member 62 has sufficient resilience or rigidity to properly clean lens 58 as well as other portions of scope 56.

As shown, for example, in FIGS. 1 and 2, each member 62 in the form of a suitable bristle 64 (shown in FIG. 1) or a suitable finger 66 (shown in FIG. 2) extends radially inward from inner wall 48 toward a longitudinal axis 70 of cannula 42 such that one or more members 62 contact scope 56 with scope 56 positioned in access channel 50 and advanced toward second opening 54 at distal portion 46. In example embodiments, members 62 are biased radially inward toward longitudinal axis 70 such that members 62 maintain an initial or first position extending radially inward toward longitudinal axis 70 when scope 56 is retracted from within distal portion 46 such that members 62 no longer contact scope 56. In certain embodiments, at least one member 62 of the plurality of members 62 is angled proximally and/or at least one member 62 of the plurality of members 62 is aligned distally with respect to a direction perpendicular to longitudinal axis 70 of cannula 42. During a surgical procedure, scope 56 is movable within access channel 50 in a reciprocating motion, e.g., in a distal direction and opposing proximal direction along longitudinal axis 70, such that members 62 contact scope 56 during such motion to clean scope 56. In a particular embodiment not shown, members 62 are operatively coupled to an actuator which is rotatably coupled to or at proximal portion 44 of cannula 42 such that members 62 are rotatable about longitudinal axis 70 as the actuator is rotated about longitudinal axis 70.

Because members 62 are located a relatively short distance from second opening 54, scope 56 is retracted a relatively short distance in order to communicate with members 62 in contrast to retracting scope 56 to proximal portion 44 located proximal relative to a patient body. It is contemplated that members 62 may be included at distal portion 46 and an additional cleaning element may be located at proximal portion 44. Further, it is contemplated that members 62 may line substantially an entirety of inner wall 48 in certain embodiments. As described herein and shown in FIGS. 1 and 2, for example, members 62 may have a default state (e.g., a first position when not influenced by scope 56) where members 62 extend angled proximally (i.e., they are tilted slightly upward with respect to horizontal from the viewpoint of FIG. 1). Additionally or alternatively, members 62 may extend angled distally (i.e., they are tilted slightly downward with respect to horizontal from the viewpoint of FIG. 1). Advantageously, the effectiveness of members 62 may be enhanced as scope 56 moves distally through cannula 42 because contact between the tips of members 62 will be more direct and friction may be increased. Members 62 may be made or formed of any suitable material including, without limitation, rubber, compliant plastic, nylon or polyester fibers, or any other suitable material(s). Members 62 with other orientations, sizes, locations, and/or materials may be additionally or alternatively used. In certain embodiments (not shown), members 62 of different sizes may be used at different locations (e.g., robust members 62 may be used for "rough cleaning" and smaller members 62 may be used for "fine cleaning" and/or polishing).

Figure 5:
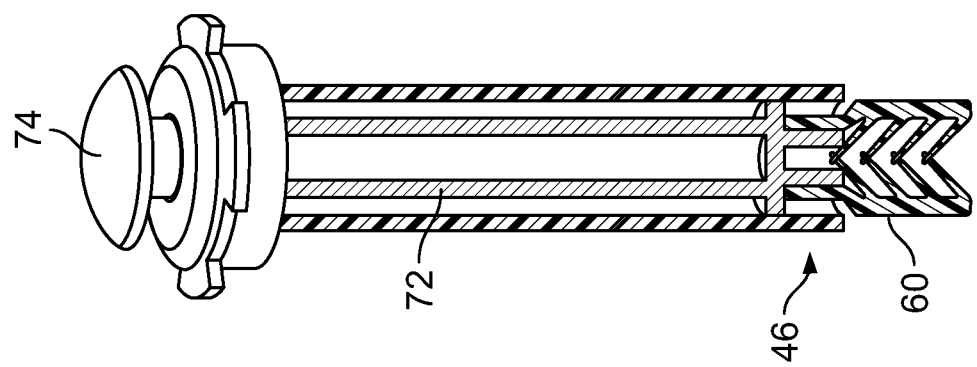
FIGS. 3-8 are sectional views of a distal portion of an example trocar assembly with an applicator inserting and positioning a cleaning element at the distal portion of the example trocar assembly in accordance with certain example embodiments.
Figure 4:
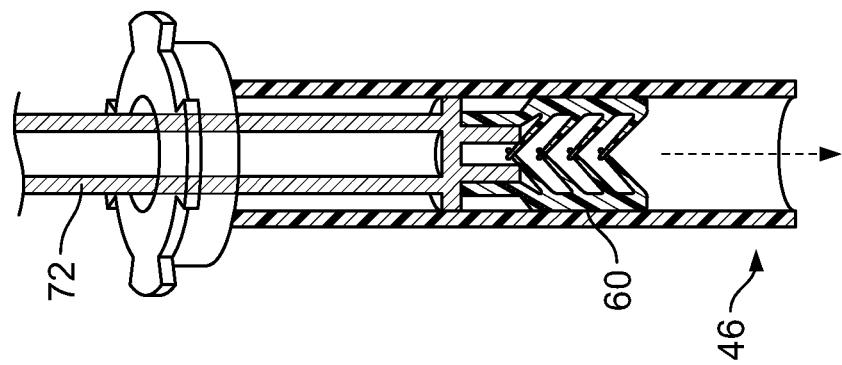
Figure 3:
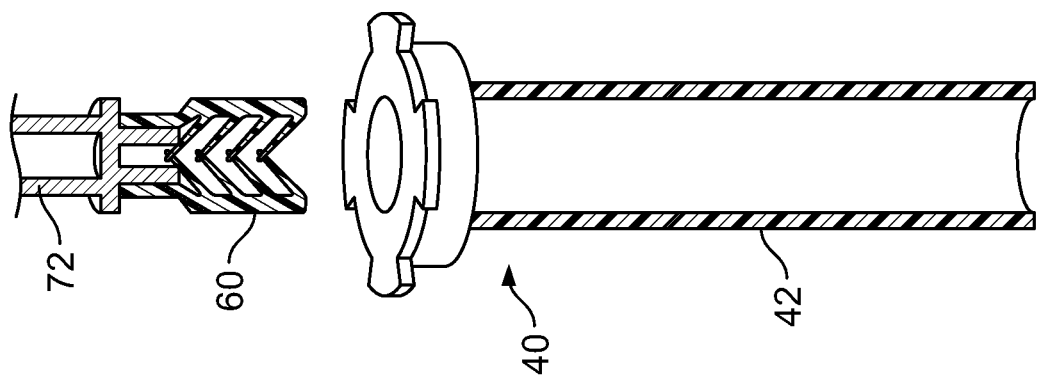
Figure 8:
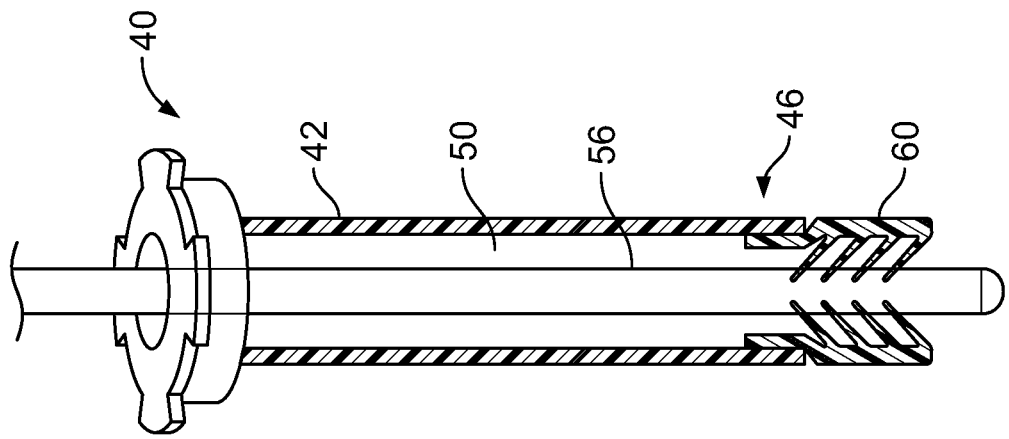
Figure 7:
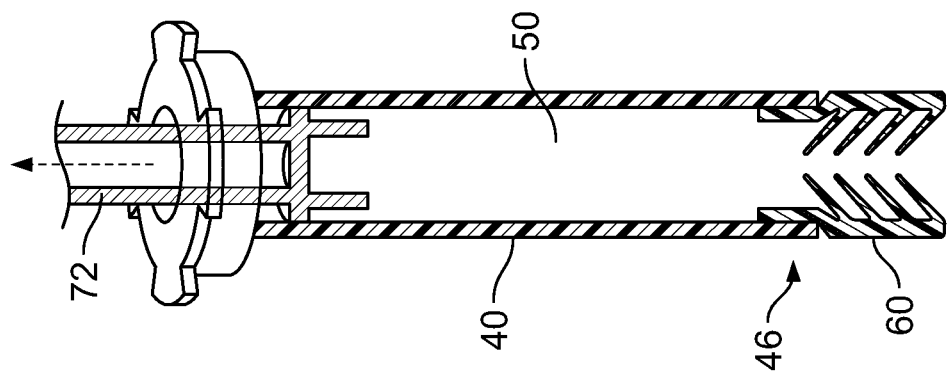
Figure 6:
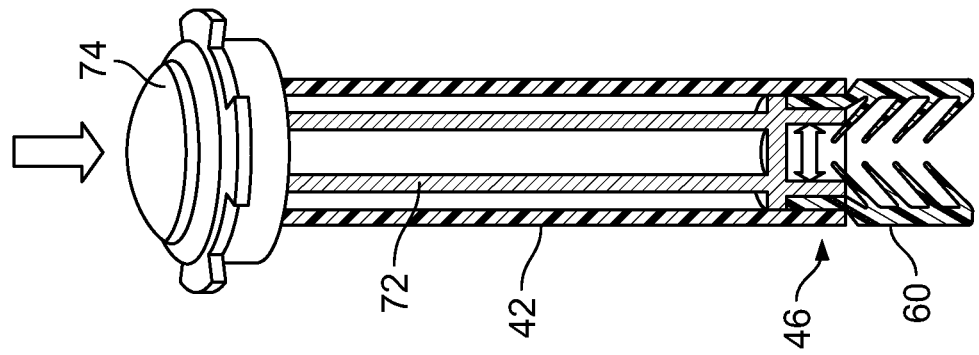

Referring further to FIGS. 3-8, in certain embodiments cleaning element 60 having a plurality of member 62 can be removably positioned at distal portion 46 of cannula 42 using a suitable applicator 72. As shown in FIGS. 3 and 4, for example, cleaning element 60 is coupled to applicator 72. Applicator 72 is configured to position cleaning element 60 at distal portion 46 of cannula 42. In example embodiments, cleaning element 60 is positioned in access channel 50 and advanced along access channel 50 toward distal portion 46 by urging applicator 72 into access channel 50. As shown in FIGS. 5 and 6, with cleaning element 60 properly positioned at distal portion 46, an actuator 74 at a proximal end of applicator 72 is operable to release or decouple cleaning element 60 from applicator 72. Applicator 72 is then removed from access channel 50, as shown in FIG. 7, to allow scope 56 to be advanced through access channel 50, as shown in FIG. 8.

Referring now to FIGS. 9-36, in certain example embodiments, cleaning element 60 is movable between a first position and a second position. In the first position, cleaning element 60 contacts at least the distal portion of scope 56 with scope 56 positioned in access channel 50. In the second position, cleaning element 60 may extend radially outward from longitudinal axis 70. Additionally or alternatively, in the second position, cleaning element 60 may extend distally outward from second opening 54 at distal portion 46.

In these example embodiments, as well as other example embodiments, cleaning element 60 includes one or more surfaces configured to contact the distal end of scope 56 with cleaning element 60 in a first position and with scope 56 positioned at distal portion 46 of access channel 50. Further, in certain embodiments, such as shown in FIGS. 9-19 and 33-36, for example, cleaning element 60 is movable between a first position and a second position via contact of cleaning element 60 with scope 56 as scope 56 moves distally or proximally through access channel 50. In the first position, cleaning element 60 may at least partially occlude second opening 54 of access channel 50.

Figure 9:
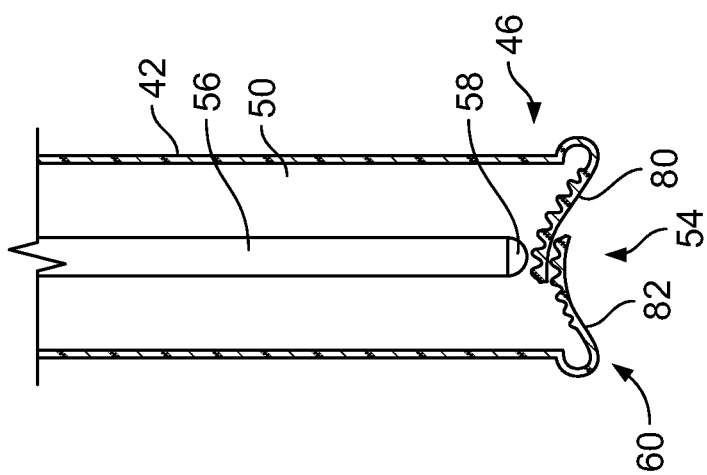
FIG. 9 is a sectional view of a distal portion of an example trocar assembly with a cleaning element in a first position in accordance with certain example embodiments.

As shown in FIG. 9, in an example embodiment, cleaning element 60 includes a plurality of portions at least partially overlapping each other to cover second opening 54 with cleaning element 60 in a first position. For example, in one embodiment, cleaning element 60 includes a first pad 80 and a second pad 82 at least partially overlapping first pad 80 to cover second opening 54 at distal portion 46 of cannula 42. With cleaning element 60 in a first position, cleaning element 60 at least partially occludes second opening 54 and contacts lens 58 of scope 56. Scope 56 may be rotated with first pad 80 and/or second pad 82 contacting lens 58 to clean lens 58. Scope 56 may be moved through access channel 50 in a distal direction to move cleaning element 60 from the first position to the second position allowing scope 56 to exit access channel 50 at distal portion 46.

Figure 11:
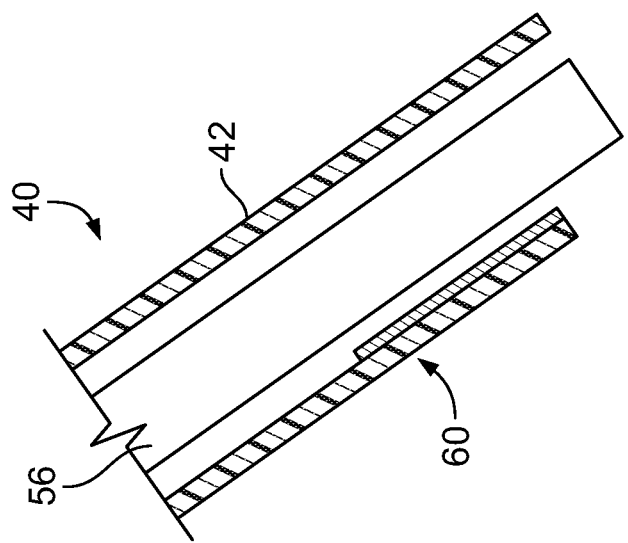
FIG. 11 is a sectional view of the distal portion of the example trocar assembly shown in FIG. 10 with the cleaning element in a second position.
Figure 10:
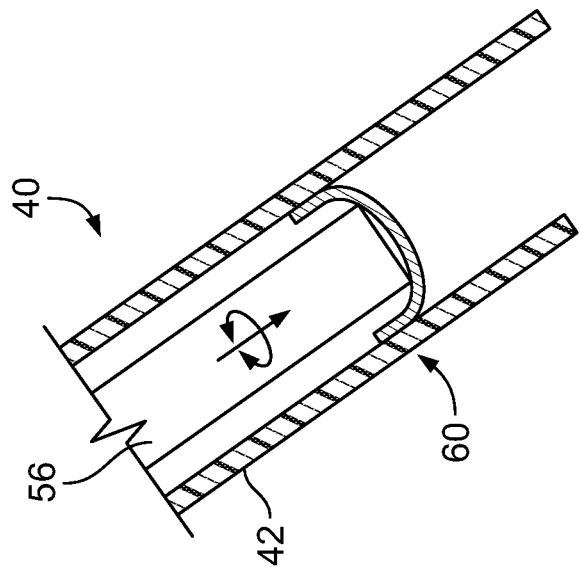
FIG. 10 is a sectional view of a distal portion of an example trocar assembly with a cleaning element in a first position in accordance with certain example embodiments.

Referring to FIGS. 10 and 11, in certain example embodiments, trocar assembly 40 includes a spring-based cleaning element 60 located within cannula 42. As shown in FIG. 10, cleaning element 60 has a first or default position in which cleaning element 60 blocks or obstructs access channel 50 extending through cannula 42 such that scope 56 traveling distally through access channel 50 contacts cleaning element 60. In this example embodiment, cleaning element 60 has a particular spring force (e.g., a force creating a tendency for cleaning element 60 to remain in the first position shown in FIG. 10) that can be overcome by a user, e.g., the surgeon performing the laparoscopic surgical procedure, urging scope 56 distally through access channel 50. Once scope 56 makes contact with cleaning element 60, and as scope 56 continues to move distally through access channel 50, cleaning element 60 may be urged into a second position, such as shown in FIG. 11. In the second position, cleaning element 60 is displaced to allow scope 56 to pass distally beyond cleaning element 60. In certain embodiments, a force required to initially displace cleaning element 60 and move cleaning element 60 from the first position to the second position may be relatively high (but still easily achievable) to ensure a sufficient degree of friction between the distal end of scope 56, e.g., lens 58, and cleaning element 60 suitable to clean lens 58, for example. However, a force required to continue to push scope 56 past cleaning element 60 once cleaning element 60 is fully displaced may be relatively low to prevent such friction from interrupting and/or substantially affecting the scope's functionality inside a patient body. While only one displaceable cleaning element 60 is shown, more than one may be included with cleaning element 60, and in some embodiments, the displaceable cleaning element 60 may substantially surround a perimeter of scope 56. It is contemplated that cleaning element 60 may be similar to a reverse-facing duckbill valve, for example.

Figure 13:
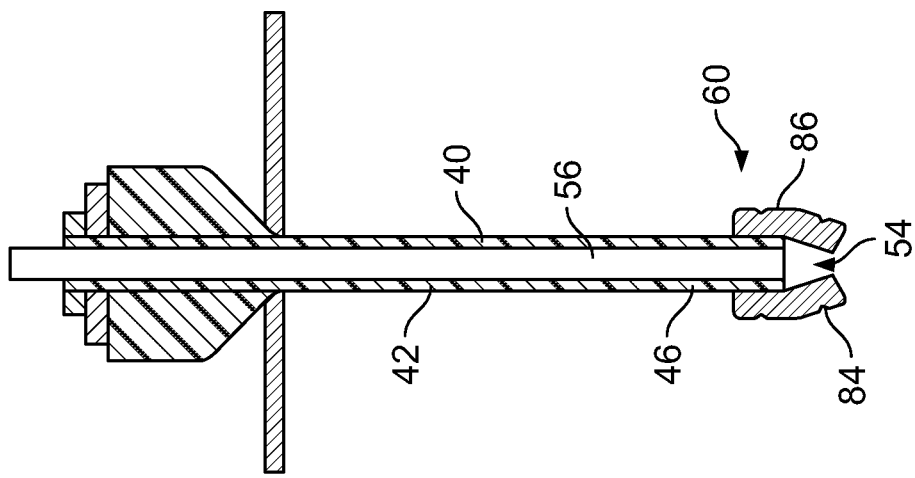
FIG. 13 is a sectional view of the example trocar assembly shown in FIG. 12 with the cleaning element in an intermediate position.
Figure 12:
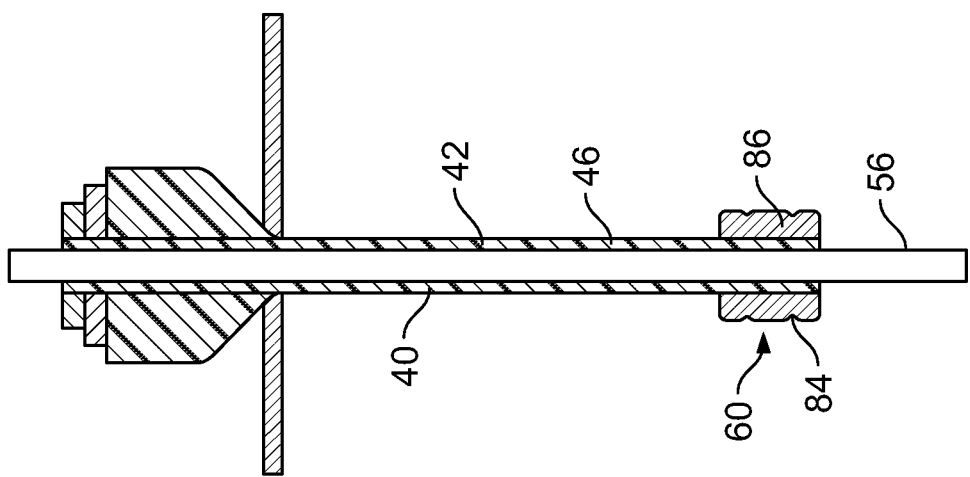
FIG. 12 is a sectional view of an example trocar assembly with a cleaning element in a second position in accordance with certain example embodiments.

FIGS. 12 and 13 show another example embodiment of trocar assembly 40 with cleaning element 60 that is displaceable by scope 56. FIG. 12 shows trocar assembly 40 with cleaning element 60 in a second position and FIG. 13 shows trocar assembly 40 with cleaning element 60 in an intermediate position as cleaning element 60 moves from the first position to the second position. In the first or default position, cleaning element 60 substantially covers second opening 54 of access channel 50. In the first position, one or more portions, such as first portion 84 and second portion 86 of cleaning element 60, include a suitable cleaning surface configured to contact scope 56 to facilitate cleaning lens 58. However, when scope 56 contacts and displaces cleaning element 60, as shown in FIGS. 12 and 13, first portion 84 and second portion 86 move radially outward and/or distally with respect to distal portion 46 of cannula 42 to allow scope 56 to extend distally from access channel 50. Cleaning element 60 may include a suitable biasing element, such as a spring or other device (e.g., a shape memory metal), to urge cleaning element 60 to return to the first position substantially covering second opening 54 when scope 56 is retracted proximally into access channel 50.

As shown in FIGS. 14-16, in certain example embodiments, trocar assembly 40 includes cleaning element 60 that is displaceable by scope 56. FIG. 14 shows distal portion 46 of trocar assembly 40 with cleaning element 60 in a first position, while FIGS. 15 and 16 show distal portion 46 of trocar assembly 40 with cleaning element 60 in the second position. Cleaning element 60 includes a plurality of members 88a, 88b, ... 88n each extending proximally into access channel 50 through second opening 54 with cleaning element 60 in the first position. Each member 88a, 88b, ... 88n includes a suitable cleaning surface configured to contact scope 56 to facilitate cleaning lens 58. It is contemplated that, for example, a medical professional may have access to proximal portion 44 of cannula 42 such that the medical professional may actuate, adjust, rotate, or otherwise move cleaning element 60 independently of scope 56. This may be advantageous where it is desired to move cleaning element 60 and scope 56 relative to one another without relying only on movement of scope 56 itself. When scope 56 contacts and displaces cleaning element 60, as shown in FIGS. 15 and 16, members 88a, 88b, . . . 88n move radially outward and/or distally with respect to distal portion 46 of cannula 42 to allow scope 56 to extend distally from access channel 50, such as shown in FIG. 15. Members 88a, 88b, . . . 88n may be made of a suitable resilient material or cleaning element 60 may include a suitable biasing element, such as a spring or other device (e.g., a shape memory metal), to urge members 88a, 88b, . . . 88n to retract into access channel 50 through second opening 54 when scope 56 is retracted proximally into access channel 50.

FIGS. 17-19 show an example embodiment of trocar assembly 40 similar to trocar assembly 40 shown in FIGS. 14-16; however, in this example embodiment, cleaning element 60 includes a collar 90 or suitable ring that is slidably positioned within access channel 50. FIG. 17 shows distal portion 46 of trocar assembly 40 with cleaning element 60 in a retracted position; FIG. 18 shows distal portion 46 of trocar assembly 40 with cleaning element 60 in a first position; and FIG. 19 shows distal portion 46 of trocar assembly 40 with cleaning element 60 in a second position. Cleaning element 60, e.g., collar 90, includes a plurality of annularly-positioned bristles 92a, 92b, . . . 92n each extending radially inward with respect to longitudinal axis 70 of cannula 42 with cleaning element 60 in the first position. Collar 90 includes one or more retaining members 94 that expand radially outward as collar 90 is advanced through distal portion 46 of cannula 42 to retain collar 90 coupled to distal portion 46. Cleaning element 60, e.g., each bristle 92 of cleaning element 60, is displaceable by scope 56. Each bristle 92a, 92b, . . . 92n includes a suitable cleaning surface configured to contact scope 56 to facilitate cleaning lens 58. It is contemplated that, for example, a medical professional may have access to proximal portion 44 of cannula 42 such that the medical professional may actuate, adjust, rotate, or otherwise move cleaning element 60 independently of scope 56. This may be advantageous where it is desired to move cleaning element 60 and scope 56 relative to one another without relying only on movement of scope 56 itself. When scope 56 contacts and displaces cleaning element 60, as shown in FIG. 19, bristles 92a, 92b, . . . 92n move radially outward and/or distally with respect to distal portion 46 of cannula 42 to allow scope 56 to extend distally from access channel 50. Bristles 92a, 92b, . . . 92n may be made of a suitable resilient material or cleaning element 60 may include a suitable biasing element, such as a spring or other device (e.g., a shape memory metal), to urge bristles 92a, 92b, . . . 92n to move radially inward toward longitudinal axis 70 when scope 56 is retracted proximally into access channel 50.

Figure 21:
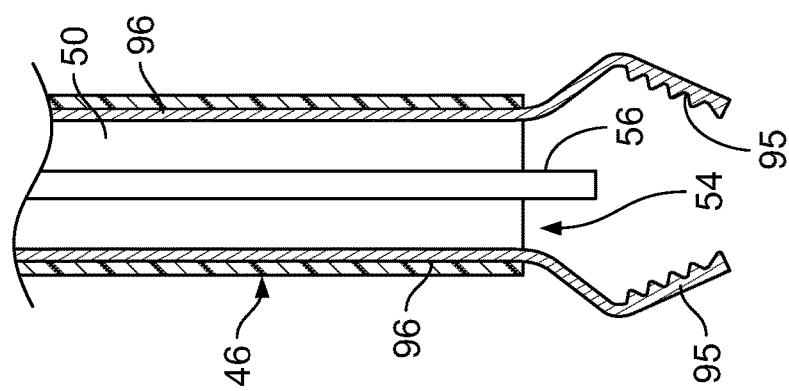
FIG. 21 is a sectional view of the distal portion of the example trocar assembly shown in FIG. 20 with the cleaning element in a second position.
Figure 20:
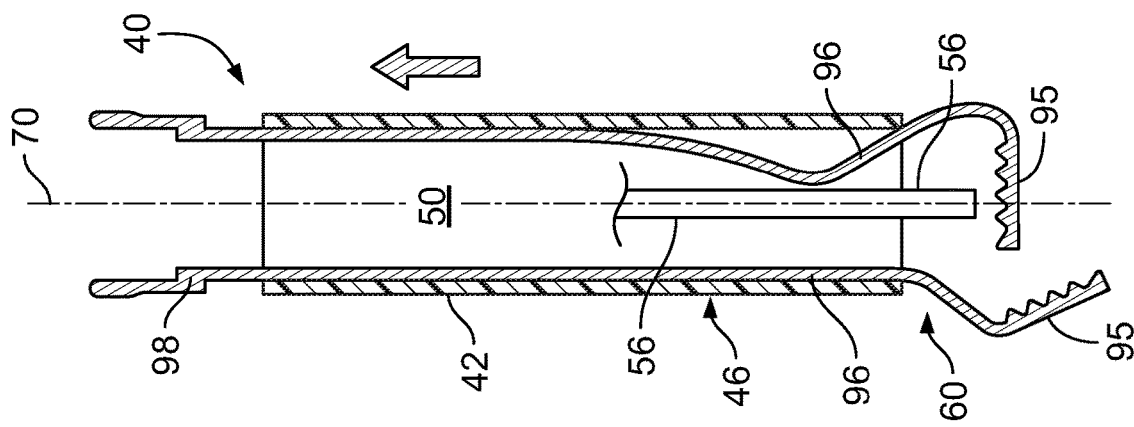
FIG. 20 is a sectional view of a distal portion of an example trocar assembly with a cleaning element in a first position in accordance with certain example embodiments.

FIGS. 20 and 21 show another example embodiment of trocar assembly 40 having cleaning element 60. FIG. 20 shows distal portion 46 of trocar assembly 40 with cleaning element 60 in a first position and FIG. 21 shows distal portion 46 of trocar assembly 40 with cleaning element 60 in a second position. In this embodiment, cleaning element 60 includes one or more deployable cleaning pads 95 having a suitable cleaning surface at a distal end of an arm 96. As shown in FIG. 20, arm 96 extends along a length of cannula 42, e.g., through access channel 50, to proximal portion 44. A control 98 operatively coupled to cleaning element 60 at or near proximal portion 44 is configured to control, e.g., manually, mechanically, or electronically, movement of arm 96 and associated cleaning pad 95 to clean the distal end of scope 56, e.g., lens 58. It is contemplated that, for example, a medical professional may have access to proximal portion 44 of cannula 42 such that the medical professional may actuate, adjust, rotate, or otherwise move cleaning element 60 independently of scope 56, as described above. For example, control 98 may include a handle accessible by a user from proximal portion 44 such that the user can manually move cleaning element 60. As such, arm 96 may be moved in a proximal direction along longitudinal axis 70 such that associated cleaning pad 95 contacts the distal end of scope 56, e.g., lens 58. In example embodiments, cleaning pads 95 are movable to a second position, for example, extending radially outward from longitudinal axis 70 and/or distally with respect to distal portion 46 of cannula 42, to allow scope 56 to extend distally from access channel 50. Cleaning pads 95 may be made of a suitable resilient material or may include a suitable biasing element, such as a spring or other device (e.g., a shape memory metal), to urge cleaning pads 95 to move radially inward toward longitudinal axis 70 when scope 56 is retracted proximally into access channel 50.

Figure 22:
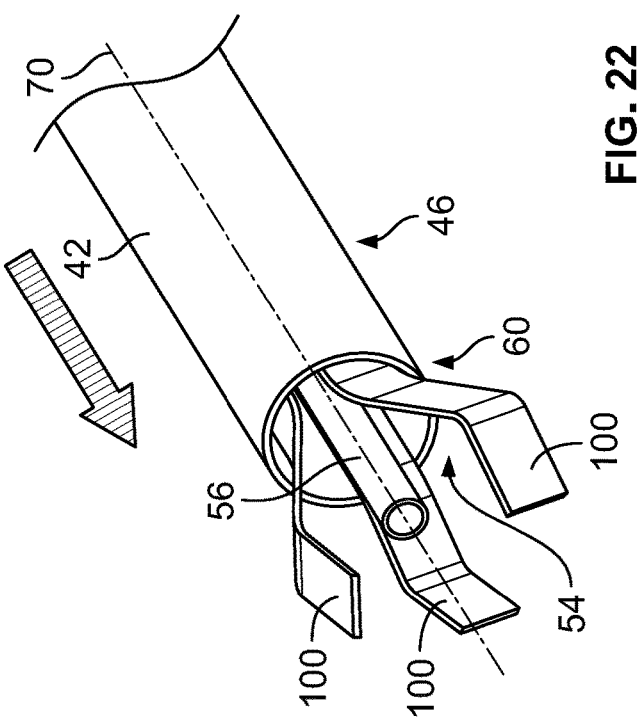
FIG. 22 is a sectional view of a distal portion of an example trocar assembly with a cleaning element in a second position in accordance with certain example embodiments.

FIG. 22 shows another example embodiment of trocar assembly 40 having cleaning element 60 in a second position. In this embodiment, cleaning element 60 includes a plurality of deployable cleaning pads 100 arranged annular about second opening 54 at distal portion 46 of cannula 42. Cleaning pads 100 can be moved together or each cleaning pad 100 can be moved independently to the first position to at least partially occlude second opening 54. In the first position, cleaning pad 100 is configured to contact at least a portion of scope 56, e.g., lens 58. The medical professional can manipulate cleaning element 60 to move one or more cleaning pads 100 against lens 58 to remove debris and clean lens 58 with control 98 (not shown in FIG. 22) operatively coupled to cleaning element 60 at or near proximal portion 44. Cleaning pads 100 are movable to a second position, as shown in FIG. 22, extending radially outward from longitudinal axis 70 and/or distally with respect to distal portion 46 of cannula 42, to allow scope 56 to extend distally from access channel 50. Cleaning pads 100 may be made of a suitable resilient material or may include a suitable biasing element, such as a spring or other device (e.g., a shape memory metal), to urge cleaning pads 100 to move radially inward toward longitudinal axis 70 when scope 56 is retracted proximally into access channel 50.

Figure 25:
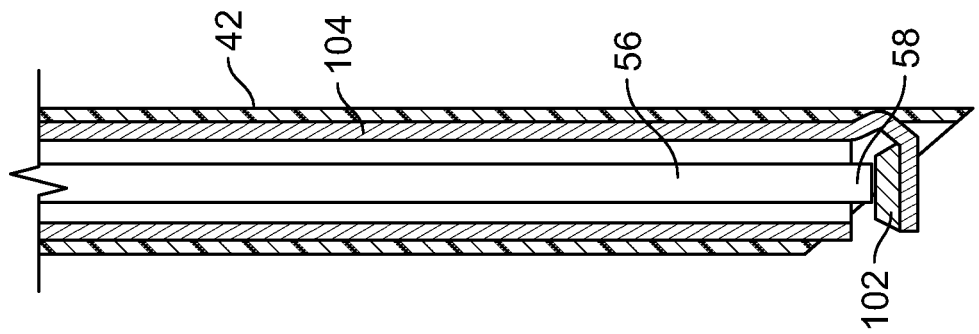
FIG. 25 is a sectional view of the distal portion of the example trocar assembly of FIG. 23 with the cleaning element in the first position.
Figure 24:
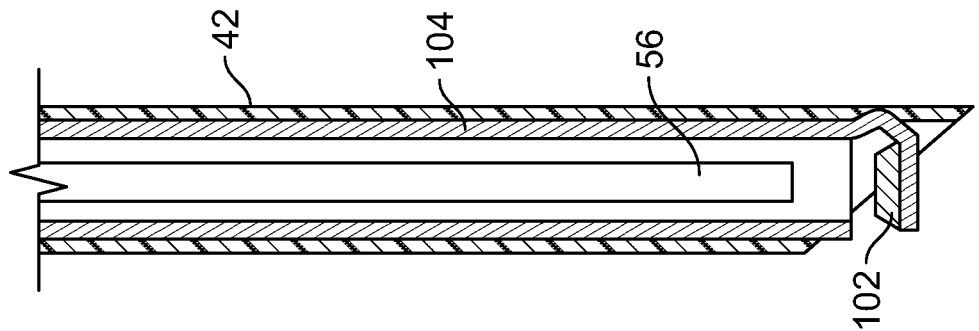
FIG. 24 is a sectional view of the distal portion of the example trocar assembly shown in FIG. 23 with the cleaning element in a first position.
Figure 23:
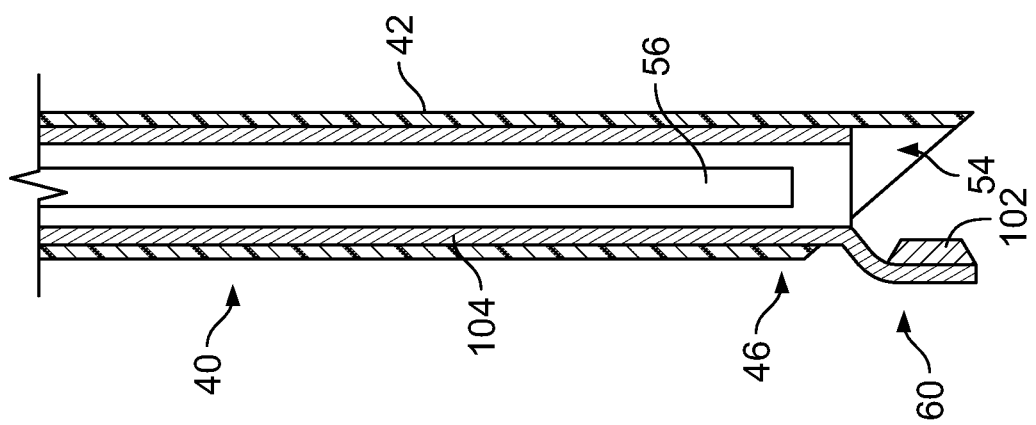
FIG. 23 is a sectional view of a distal portion of an example trocar assembly with a cleaning element in a second position in accordance with certain example embodiments.

Referring now to FIGS. 23-28, in an example embodiment, trocar assembly 40 includes cleaning element 60 having one or more deployable cleaning pads 102 having a suitable cleaning surface at a distal end of an arm 104. FIG. 23 shows distal portion 46 of trocar assembly 40 with cleaning element 60 in a second position, while FIGS. 24 and 25 show distal portion 46 with cleaning element 60 in the first position. Referring further to FIGS. 26-28, arm 104 extends along a length of cannula 42, e.g., through access channel 50, to proximal portion 44. An actuator, such as a lever 106 shown in FIGS. 27 and 28, at or near proximal portion 44 of cannula 42, is operatively coupled to cleaning element 60 and configured to move, e.g., rotate cleaning element 60 in a clockwise and/or counterclockwise direction and/or translate cleaning element 60 in a distal direction and/or an opposing proximal direction along longitudinal axis 70, and between the first position and the second position. For example, lever 106 at or near proximal portion 44 is operatively coupled to arm 104 such that rotation of lever 106 deploys cleaning pad 102 and, with cleaning pad 102 in the first position contacting lens 58, for example, lever 106 is rotated to move cleaning pad 102 in an associated direction with respect to lens 58 to clean the distal end of scope 56, e.g., lens 58. It is contemplated that, for example, a medical professional may have access to proximal portion 44 of cannula 42 such that the medical professional may actuate, adjust, rotate, or otherwise move cleaning element 60 independently of scope 56, as described above. In example embodiments, cleaning pad 102 is movable to a second position, as shown in FIG. 23, extending distally with respect to distal portion 46 of cannula 42, to allow scope 56 to extend distally from access channel 50.

FIGS. 29-32 show another example embodiment of trocar assembly 40 having cleaning element 60. FIGS. 29 and 31 show distal portion 46 of trocar assembly 40 with cleaning element 60 in a second position and FIG. 30 shows distal portion 46 of trocar assembly 40 with cleaning element 60 in a first position. FIG. 32 shows a biasing element suitable for use with cleaning element 60 in this example embodiment. Cleaning element 60 includes a cap 107 movably coupled at distal portion 46 of cannula 42. Cap 107 is movable between a first position, as shown in FIG. 30, configured to cover second opening 54 at distal portion 46 of cannula 42 and a second position, as shown in FIGS. 29 and 31, configured to provide communication with access channel 50 through second opening 54 to allow scope 56 to move through access channel 50 and extend distally from cannula 42. In this embodiment, cleaning element 60 includes a cleaning pad 108 in cap 107 having a suitable cleaning surface. With cleaning element 60 in the first position, cleaning pad 108 is configured to contact the distal end of scope 56, e.g., lens 58. As cannula 42 is rotated with respect to scope 56, cleaning pad 108 to clean the distal end of scope 56, e.g., lens 58. It is contemplated that, for example, a medical professional may have access to proximal portion 44 of cannula 42 such that the medical professional may actuate, adjust, rotate, or otherwise move cleaning element 60 independently of scope 56, as described above. Cleaning element 60 may be made of a suitable resilient material or may include a suitable biasing element 109, such as a spring 110 shown in FIG. 32 or another suitable element (e.g., a shape memory metal), to bias cap 107 to move toward the first position when scope 56 is retracted proximally into access channel 50.

Referring to FIGS. 33 and 34, in another example embodiment, trocar assembly 40 includes cleaning element 60 having a cleaning pad 111 initially positioned within access channel 50 that is displaceable by scope 56. FIG. 33 shows distal portion 46 of trocar assembly 40 with cleaning pad 111 positioned in access channel 50 and cleaning element 60 in a first position. FIG. 34 shows distal portion 46 of trocar assembly 40 with cleaning pad 111 displaced by scope 56 and cleaning element 60 in a second position, allowing scope 56 to move through access channel 50. In the first or default position, one or more flanges, e.g., a first flange 112 and an opposing second flange 114 of cleaning element 60 shown in FIGS. 33 and 34, maintain cleaning element 60 in the first position. Cleaning element 60 includes cleaning pad 111 having a suitable cleaning surface configured to contact scope 56 to facilitate cleaning lens 58. A central opening 116, e.g., a slit, is formed through cleaning pad 111 such that when scope 56 contacts cleaning pad 111 with sufficient force, scope 56 passes through central opening 116 to extend distally from access channel 50 as shown in FIG. 34. As scope 56 extends through cleaning pad 111, first flange 112 and second flange 114 move radially outward and/or distally with respect to distal portion 46 of cannula 42 to allow scope 56 to extend distally from access channel 50. In this embodiment, components of cleaning element 60, e.g., cleaning pad 111, first flange 112, and second flange 114, are made of a suitable resilient material such that cleaning pad 111, first flange 112, and second flange 114 return to an initial position substantially covering second opening 54 when scope 56 is retracted proximally into access channel 50 and cleaning element 60 is in the first position.

Referring to FIGS. 35 and 36, in another example embodiment, trocar assembly 40 includes cleaning element 60 having a cleaning sphere 118 initially positioned within access channel 50 that is displaceable by scope 56. FIG. 35 shows distal portion 46 of trocar assembly 40 with cleaning sphere 118 positioned in access channel 50 and cleaning element 60 in a first position. FIG. 36 shows distal portion 46 of trocar assembly 40 with cleaning sphere 118 displaced by scope 56 and cleaning element 60 positioned in a second position, allowing scope 56 to move through access channel 50. In the first or default position, one or more flanges, e.g., a first flange 120 and an opposing second flange 122 of cleaning element 60 shown in FIGS. 35 and 36, maintain cleaning element 60 in the first position. Cleaning sphere 118 has a suitable cleaning surface configured to contact scope 56 to facilitate cleaning lens 58. As scope 56 contacts cleaning pad 111 with sufficient force, scope 56 moves cleaning sphere 118 in a transverse direction toward inner wall 48 of access channel 50 to allow scope 56 to extend distally from access channel 50 as shown in FIG. 36. As scope 56 extends through cleaning element 60, first flange 120 and second flange 122 move radially outward and/or distally with respect to distal portion 46 of cannula 42 to allow scope 56 to extend distally from access channel 50. In this embodiment, components of cleaning element 60, e.g., cleaning sphere 118, first flange 120, and second flange 122, are made of a suitable resilient material such that cleaning pad 118, first flange 120, and second flange 122 return to an initial position substantially covering second opening 54 when scope 56 is retracted proximally into access channel 50 and cleaning element 60 is in the first position.

Referring now to FIGS. 37-40, in example embodiments, scope 56 includes cleaning element 60 having an expandable pad 140 initially positioned within second opening 54 to at least partially occlude second opening 54 with cleaning element 60 in a second position. Expandable pad 140 is displaceable by scope 56. FIG. 37 shows distal portion 46 with expandable pad 140 positioned in second opening 54 and cleaning element 60 in the first position. FIGS. 38 and 39 show distal portion 46 shown in FIG. 37 as cleaning element 60 moves from the first position to a second position. FIG. 40 shows distal portion 46 with expandable pad 140 displaced by scope 56 and cleaning element 60 in a second position, allowing scope 56 to move through second opening 54 to extend distally with respect to distal portion 46. Expandable pad 140 has a suitable cleaning surface configured to contact scope 56 to facilitate cleaning lens 58.

A central opening 144, e.g., a slit, is formed through expandable pad 140 such that when lens 58 contacts expandable pad 140 with sufficient force, lens 58 passes through central opening 144 to extend distally from second opening 54 as shown in FIG. 40. As lens 58 passes through central opening 144, expandable pad 140 removes condensation and/or debris from lens 58. Expandable pad 140 is moveable in a radially outward direction with lens 58 extending into central opening 144. In this embodiment, expandable pad 140 is made of a suitable resilient material such that expandable pad 140 returns to an initial position substantially covering second opening 54 when scope 56 is retracted proximally into access channel 50 and cleaning element 60 is in the first position.

In example embodiments, a method for cleaning a distal end of a scope positioned within an access channel of a trocar includes coupling or positioning a cleaning element at a distal portion of a cannula of the trocar assembly. The distal portion is configured to extend into a patient body. The cannula defines an access channel between a first opening at the proximal portion and a second opening at the distal portion, wherein the access channel is configured to receive a scope such that the scope can be maneuvered through the access channel to a location within the patient body. At least a distal end of the scope is cleaned with the cleaning element by moving the cleaning element with respect to the distal end of the scope.

As described herein, example trocar assemblies for use during a laparoscopic procedure include a cannula having a distal end for placement into a patient body during the laparoscopic procedure. The distal end of the cannula may include a beveled or sharpened end to facilitate entry of the cannula into the patient body. An obturator may additionally or alternatively be included. The cannula may include certain surface characteristics, such as threads or ridges, to enhance the stability of the trocar assembly when inserted into a body incision.

The cannula may include or may be in fluid communication with a chamber defined by a proximal portion of the trocar assembly. The chamber may have a proximal opening configured to receive medical devices used during laparoscopic surgery, including, without limitation, graspers, dissectors, needles, scissors, clamps, electrodes, forceps, a camera, and/or a laparoscope (a "scope"). A valve may be located in the proximal opening and may form a seal or fluid barrier between the chamber and an external environment (e.g., the ambient room environment). Alternatively or in addition, the valve may be located in another location (such as at a distal opening of the cannula). It may be advantageous for at least one valve to be located at a the proximal opening such that a lens of a scope does not have to pass through the valve prior to cleaning, thereby reducing or eliminating the chance of materials from the valve dirtying the scope's lens after cleaning.

The chamber may be subjected to a continuous sterile and pressurized environment that extends through the cannula and to the body cavity (herein referred to as the "internal environment" even though the continuous region may extend external of the patient body wall, e.g., within the trocar assembly). This may be advantageous if maintaining insufflation of the body cavity is desired during all operation—including cleaning—of a trans-trocar-located scope or other device. Further, the controlled environment of the chamber may reduce fogging of a scope by eliminating or reducing temperature changes and/or changes in humidity.

The valve (which may include more than one valve) may include a particular structure that allows certain medical devices to pass through the proximal opening and into the chamber while maintaining the seal or fluid barrier. For example, the valve may include a duckbill seal, an annular seal structure, or both, but other suitable structures may additionally or alternatively be included. The valve may be formed with a compliant material such that it expands or contracts as necessary for compatibility with scopes of different sizes. For example, on the Shore Hardness Scale, the valve may be formed of a material with a hardness between about Shore A 20 to about Shore A 80, such as from about Shore A 30 to about Shore A 60.

An insufflation inlet may communicate with the chamber and may be configured to control the pressure and other characteristics (e.g., temperature, composition of the atmosphere), which may be advantageous for providing precise control of insufflation of a body cavity during the laparoscopic procedure. The insufflation inlet may include an insufflation valve, and may be in fluid communication with a pump or other suitable pressure source. Advantageously, the flow of gasses or other contents received into the chamber through the insufflation inlet may be introduced in a manner such that the effect of the flow across cleaning element is reduced or eliminated. For example, when the cleaning element (which is described in detail above) is wetted with a cleaning fluid, concerns of increased evaporation due to fluid flow over the cleaning element may be alleviated.

The trocar assembly may provide an entry or point of access into the body for a scope. In non-limiting embodiments, the scope may include a commercially-available rigid laparoscope with a 5 millimeter (mm) or a 10 mm diameter (or any other suitable diameter) with either a non-angled lens or an angled lens, which may be angled at 30 degrees, 45 degrees, or 50 degrees, for example, with respect to the longitudinal axis of the scope. At least a distal end of the scope may include one or more elements designed to magnify, reflect, illuminate, and/or capture images of internal body areas under treatment, and then transmit those images back to the medical professional controlling the procedure (herein referred to as a "viewing element"). The scope may be inserted into the proximal opening of the chamber, may extend through the chamber, and may extend through into the cannula through a distal opening in the bottom wall of the chamber, where the distal opening is in fluid and mechanical communication with the cannula. The scope may further extend distally to the distal end of the cannula and into the body cavity. In some embodiments, a sleeve (not shown, but readily understood as a lining layer) may be located within the cannula, and the scope may pass through the sleeve. Once deployed, the scope may be manipulated by the medical professional moving it distally/proximally, angling it, and/or by rotating it into a particular orientation. Typically, during laparoscopic procedures, scopes can become obstructed when debris (e.g., condensation, displaced tissue, bodily fluids) are encountered and accumulate on a lens of the scope, which may compromise the image or video feed provided to the medical professional.

The surface of the cleaning element may facilitate removal of obstructions from the scope without necessitating removal of the scope from the internal environment. Advantageously, lengthy interruptions (and therefore increased surgical and anesthesia time) due to removing and/or replacing an obstructed scope may be reduced or eliminated. Further, the distal end of the scope may remain in the sterile internal environment during cleaning, which may advantageously alleviate concerns related to loss of sterility within the internal environment due to the removal and re-entry of the scope one or more times for cleaning purposes. Keeping the scope within the internal environment may also reduce or eliminate debris in the form of fogging or condensation caused by exposure to pressure and/or temperature changes when switching between environments. It should also be understood that certain advantages of the present embodiments are generally described as relating to a scope for explanation purposes and may also extend to other types of instruments used during surgical procedures, and therefore "scope" should be understood as including any suitable medical device used during laparoscopic surgery when described in the context of the present embodiments, unless clearly excluded.

The cleaning element may incorporate any suitable structures, materials, and/or cleaning solutions for removing obstructions from the scope. The cleaning element may have a unitary construction, or alternatively may have multiple surfaces or layers with different cleaning characteristics or properties for facilitating multiple treatments. For example, it is contemplated that the cleaning element may have a first region with an abrasive surface for breaking up potential obstructions, a second region including a liquid, a gel, or other material for dissolving or washing away the obstructions, and a third region with an absorbent or adsorbent surface for removing any remaining residue.

The cleaning element may include any suitable cleaning structures or materials, such as sponges, foams (e.g., reticulated or non-reticulated foamed plastic polymers forming open-cell, semi-open cell, or closed-cell foam structures), fibrous materials (e.g., materials with natural (e.g., cellulosic) and/or synthetic fibers), microfiber or wipe materials (e.g., polyethers, polyamides, polyesters, and/or blends of each in a woven or non-woven construction with split or non-split fibers), hydrophilic or hydrophobic materials, fluids, gases, bristles, films, etc. The structures and/or materials of the cleaning element may include hydrophobic properties to assist in absorbing and wicking of various bodily fluids and/or lipophilic characteristics for increased absorption of oils or fats. The cleaning element may be capable of absorbing at least 5 times its original weight of fluids, such as about 15 times its original weight (or more). When the cleaning element includes pores, consistent or variable pore sizes may be consistently or randomly dispersed (or layered) in certain configurations for suitable absorption properties (for example, a the cleaning element may include a micro-porous foam with about 4 pores per inch to about 100 pores per inch). The cleaning element may have a firmness/compliance of about 2 lbs/50 in$^2$ to about 80 lbs/50 in$^2$, and preferably about 6 lbs/50 in$^2$ to about 45 lbs/50 in$^2$ (when tested at 25% deflection on a 20 inch by 20 inch by 4 inch specimen). The material(s) of the cleaning element may be formed of a material suitable for use in a medical device (e.g., with suitable biocompatibility, non-linting/no particulate, tear resistance, sterilization or other chemical/solvent compatibility, and radiation stability).

The cleaning element may be multi-layered in some embodiments. For example, a first layer may be configured to absorb a fluid obstruction located on the scope, and a second layer may be configured to retain or discard that fluid. In some embodiments, the first layer may include an open-cell foam with relatively low density (such as polyurethane or silicone foam) that may be used to effectively and quickly absorb (or wick, etc.) the obstructing fluid, and the second layer may include higher-density foam for effectively retaining the fluid. The second layer may be located beneath (e.g., covered by) the first layer, for example. Fibrous materials such as terrycloth and microfiber cloths may additionally or alternatively be used and may be advantageous for providing a streak-free lens surface when wiped against the scope. The solid materials of the cleaning element may be combined or "wetted" with a cleaning fluid, such as an anti-fog fluid, sterile water, saline, or a detergent, for example, which may facilitate the removal of fatty smudges and dried-on debris.

In the event the medical professional's visibility becomes compromised due to obstruction of the scope during surgery, the scope may be retracted proximally such that the distal end of the scope is located within the chamber. The distal end (or other location) may then be wiped or swept by pressing and/or rubbing the distal end of the scope on the cleaning element to remove obstructions. As explained above, this cleaning procedure may advantageously be completed without removing the scope from the internal environment in the trocar assembly. In certain embodiments, the cannula may be formed of a transparent or translucent material. When the scope is located in the trocar assembly, the scope (which often includes a light) may illuminate the cannula to increase visibility.

In some embodiments, the cleaning element may be selectable, removable, and/or replaceable. Thus, the trocar assembly may be capable of allowing access into the chamber (e.g., in an operating room prior to a surgery) such that a medical professional can select an appropriate version of the cleaning element and then use that cleaning element with the trocar assembly during the procedure. The cleaning element may additionally or alternatively be replaced during a medical procedure (e.g., if it becomes soiled), and/or may be replaced between medical procedures during reprocessing of the trocar assembly if the trocar assembly is reusable.

After completion of the cleaning procedure, the distal end of the scope may be again advanced through the cannula and out beyond the cannula distal end to restore the image or video feed provided by the scope. Those of skill in the art will appreciate that existing scopes and potential scope designs include at least one non-longitudinal, distal-end-facing surface of the distal end that may be generally or exactly perpendicular to the longitudinal axis of the scope, or which distal-facing surface may be configured at a non-perpendicular angle relative to the longitudinal axis (e.g., 30 degrees off-perpendicular, 45 degrees off-perpendicular). It is further contemplated that the distal-facing surface of the scope may be flat/planar, concave, or convex relative to the major plane of that face. The term "non-longitudinal, distal-end-facing surface" is meant to include the operative end face(s) of a scope in distinction from the longitudinal lateral sides of the scope, which will generally be columnar or cylindrical. Thus, as described in more detail below, the surface characteristics of the cleaning element may be shaped or otherwise configured for compatibility with a variety of distal-facing surfaces of the scope.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. This specifically includes that the structure, location, and mechanisms of the disclosed cleaning elements and related structures in the different embodiments illustrated and described with reference to the drawing figures may be combined and elements interchanged within the level of skill in the art as informed by this application, and within the scope of the present claims, which includes that a variety of disclosed individual cleaning element components dimensioned for use encompassed within in laparoscopy trocars may be configured as separable/replaceable components of a larger trocar assembly. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A trocar assembly, comprising:
   a proximal portion;
   a cannula extending between the proximal portion and a distal portion of the trocar assembly opposite the proximal portion, the distal portion configured to extend into a patient body, the cannula defining an access channel between a first opening at the proximal portion and a second opening at the distal portion, wherein the access channel is configured to receive a scope such that the scope can be maneuvered through the access channel to a location within the patient body;
   a cleaning element at the distal portion, wherein the cleaning element is configured to contact at least a distal end of the scope with the cleaning element in a first position;
   an applicator that extends through the access channel and moves the cleaning element within the access channel between the first position and a second position; and
   an actuator at the proximal portion of the cannula, the applicator is operatively coupled to the cleaning element and configured to move the cleaning element between the first position and the second position, the actuator operable to release or decouple the cleaning element from the applicator.

2. The trocar assembly of claim 1, wherein in the first position, the cleaning element contacts at least the distal portion of the scope with the scope positioned in the access channel.

3. The trocar assembly of claim 2, wherein in the first position, the cleaning element extends radially inward toward a longitudinal axis of the cannula.

4. The trocar assembly of claim 2, wherein in the second position, the cleaning element is moved by the applicator to a location distal from the second opening.

5. The trocar assembly of claim 1, wherein the cleaning element comprises a plurality of members extending radially inward toward a longitudinal axis of the cannula such that the plurality of members contact the scope with the scope positioned in the access channel.

6. The trocar assembly of claim 5, wherein the plurality of members are biased radially inward toward the longitudinal axis of the cannula.

7. The trocar assembly of claim 5, wherein each member of the plurality of members is formed of a compliant material such that each member is movable upon contacting the scope.

8. The trocar assembly of claim 5, wherein each member of the plurality of members extends from an inner wall of the cannula defining the access channel toward the longitudinal axis of the cannula.

9. A trocar assembly, comprising:
   a cannula having a proximal portion and an opposing distal portion, the distal portion configured to extend into a patient body, the cannula defining an access channel between the proximal portion and the distal portion, wherein the access channel is configured to receive a scope such that the scope can be maneuvered through the access channel to a location within the patient body;
   a cleaning element at the distal portion, wherein the cleaning element is configured to contact at least a distal end of the scope;
   an applicator that extends through the access channel and moves the cleaning element within the access channel between a first position and a second position; and
   an actuator configured to connect and disconnect the applicator from the cleaning element.

10. The trocar assembly of claim 9, wherein in the first position, the cleaning element contacts at least the distal portion of the scope with the scope positioned in the access channel.

11. The trocar assembly of claim 10, wherein in the first position, the cleaning element extends radially inward toward a longitudinal axis of the cannula.

12. The trocar assembly of claim 10, wherein in the second position, the cleaning element extends radially outward from a longitudinal axis of the cannula.

13. The trocar assembly of claim 10, wherein in the second position, the cleaning element is moved by the applicator to a location distal from an opening at the distal portion.

14. The trocar assembly of claim 10, wherein the applicator is operatively coupled to the cleaning element and configured to move the cleaning element between the first position and the second position manually using an actuator.

15. The trocar assembly of claim 9, wherein the cleaning element comprises a plurality of members extending radially inward toward a longitudinal axis of the cannula such that the plurality of members contact the scope with the scope positioned in the access channel.

16. The trocar assembly of claim 15, wherein the plurality of members are biased radially inward toward the longitudinal axis of the cannula.

17. The trocar assembly of claim 15, wherein at least one member of the plurality of members is angled proximally with respect to a direction perpendicular to the longitudinal axis of the cannula.

18. The trocar assembly of claim 15, wherein each member of the plurality of members is formed of a compliant material such that each member is movable upon contacting the scope.

19. The trocar assembly of claim 15, wherein each member of the plurality of members extends from an inner wall of the cannula defining the access channel toward the longitudinal axis of the cannula.

20. The trocar assembly of claim 9, wherein in the first position, the cleaning element at least partially occludes a distal opening of the access channel.

21. The trocar assembly of claim 9, wherein the applicator includes a handle accessible by a user from the proximal portion such that the user can manually move the cleaning element.

22. A method for cleaning a distal end of a scope positioned within an access channel of a trocar assembly, said method comprising:
   coupling a cleaning element at a distal portion of a cannula of the trocar assembly using an applicator that extends through the access channel and moves the cleaning element within the access channel to the distal portion, the distal portion configured to extend into a patient body, the cannula defining an access channel between a first opening at a proximal portion of the cannula and a second opening at the distal portion, wherein the access channel is configured to receive a scope such that the scope can be maneuvered through the access channel to a location within the patient body;

cleaning at least a distal end of the scope with the cleaning element by moving the cleaning element with respect to the distal end of the scope; and disconnecting the applicator from the cleaning element using an actuator configured to connect and disconnect the applicator from the cleaning element.

\* \* \* \* \*